United States Patent
Locke et al.

(10) Patent No.: US 10,786,607 B2
(45) Date of Patent: Sep. 29, 2020

(54) MANUALLY-ACTUATED REDUCED PRESSURE TREATMENT SYSTEM WITH AUDIBLE LEAK INDICATOR

(71) Applicant: KCI Licensing, Inc., San Antonio, TX (US)

(72) Inventors: Christopher Brian Locke, Bournemouth (GB); Richard Daniel John Coulthard, Verwood (GB); David George Whyte, Wareham (GB)

(73) Assignee: KCI Licensing, Inc., San Antonio, TX (US)

( * ) Notice: Subject to any disclaimer, the term of this patent is extended or adjusted under 35 U.S.C. 154(b) by 476 days.

(21) Appl. No.: 15/875,110

(22) Filed: Jan. 19, 2018

(65) Prior Publication Data
US 2018/0207329 A1    Jul. 26, 2018

Related U.S. Application Data

(63) Continuation of application No. 14/156,256, filed on Jan. 15, 2014, now Pat. No. 9,907,889.
(Continued)

(51) Int. Cl.
*A61M 35/00* (2006.01)
*A61M 1/00* (2006.01)
(Continued)

(52) U.S. Cl.
CPC .......... *A61M 1/005* (2014.02); *A61M 1/0025* (2014.02); *A61M 1/0039* (2013.01);
(Continued)

(58) Field of Classification Search
CPC ......... A61M 35/00; A61M 1/00; A61F 13/00; A61F 13/02; A61B 5/00; A61L 15/16; A61K 9/70
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound control and Treatment: Clinical Experience; Annals of Plastic Surgery; vol. 38, No. 6, Jun. 1997; pp. 563-576.

(Continued)

*Primary Examiner* — Tatyana Zalukaeva
*Assistant Examiner* — Ilya Y Treyger

(57) ABSTRACT

Illustrative embodiments of new and useful systems and methods for reduced-pressure therapy are described. One example embodiment is a manually-actuated pump for applying reduced-pressure therapy. The pump generally comprises a charging chamber, a regulated chamber, and a regulator passage between the charging chamber and the regulated chamber. A valve body controls fluid communication through the regulator passage, and a regulator spring may be engaged with the valve body to bias the valve body against a differential between a pressure in the regulated chamber and an ambient pressure. The regulator passage may have a bore size adapted deflect the valve body to cause an audible indication of a leak.

20 Claims, 17 Drawing Sheets

Related U.S. Application Data

(60) Provisional application No. 61/753,356, filed on Jan. 16, 2013.

(51) Int. Cl.
    *A61F 13/02*      (2006.01)
    *A61F 13/00*      (2006.01)
    *A61B 5/00*      (2006.01)
    *A61L 15/16*      (2006.01)
    *A61K 9/70*      (2006.01)

(52) U.S. Cl.
    CPC ....... *A61M 1/0088* (2013.01); *A61M 2205/15* (2013.01); *A61M 2205/183* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,104,005 A * | 8/1978 | Poirier ............... F04B 43/10 285/281 |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,444,611 B2 * | 5/2013 | Wilkes ................. A61F 13/067 604/305 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0064132 A1 * | 4/2004 | Boehringer ......... A61M 1/0031 604/543 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |

(56) References Cited

FOREIGN PATENT DOCUMENTS

| WO | 96/05873 A1 | 2/1996 |
|---|---|---|
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

MANUALLY-ACTUATED REDUCED PRESSURE TREATMENT SYSTEM WITH AUDIBLE LEAK INDICATOR

The present invention is a continuation of U.S. patent application Ser. No. 14/156,256, filed Jan. 15, 2014, which claims the benefit, under 35 USC § 119(e), of the filing of U.S. Provisional Patent Application No. 61/753,356, entitled "MANUALLY-ACTUATED REDUCED PRESSURE TREATMENT SYSTEM WITH AUDIBLE LEAK INDICATOR," filed Jan. 16, 2013, by Locke et al., which is incorporated herein by reference for all purposes.

BACKGROUND OF THE INVENTION

1. Field of the Invention

The subject matter described herein relates generally to reduced pressure treatment systems. More particularly, but without limitation, the subject matter relates to a manually-actuated reduced pressure treatment system having capabilities for providing a regulated pressure to a tissue site and an audible indication of a leak.

2. Description of Related Art

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure is commonly referred to as "reduced-pressure therapy," but may also be known by other names, including "negative pressure wound therapy," "vacuum-assisted closure," or "vacuum therapy," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure systems, components, and processes continues to present significant challenges to manufacturers, healthcare providers, and patients.

SUMMARY

Illustrative embodiments of new and useful systems and methods for reduced-pressure therapy are described herein. One example embodiment is a manually-actuated pump for applying reduced-pressure therapy, which generally comprises a charging chamber, a regulated chamber, and a regulator passage between the charging chamber and the regulated chamber. A valve body is adapted to control fluid communication through the regulator passage, and a regulator spring may be engaged with the valve body to bias the valve body against a differential between a pressure in the regulated chamber and an ambient pressure. The regulator passage may have a bore size adapted to deflect the valve body, leaving a gap between the valve body and the regulator passage to cause an audible indication of a leak above a threshold. The gap in some example embodiments may be less than 0.1 mm, and the bore size preferably has a diameter in a range of about 1 mm to about 1.5 mm. A conduit may also be coupled to the outlet port, and the conduit preferably has a lumen with a diameter of about 1.2 mm.

Other illustrative embodiments of an apparatus are described having a piston chamber having a closed end, a piston disposed within the piston chamber and being movable between an extended position and a compressed position, a charging chamber disposed between the piston and the closed end, and a regulated chamber. A biasing member may be adapted to bias the piston toward the extended position, and a valve member can be adapted to allow fluid to exit the charging chamber as the piston moves toward the compressed position and to prevent fluid from entering the charging chamber as the piston moves toward the extended position. A regulator member may be provided to regulate fluid communication through a passage between the charging chamber and the regulated chamber, wherein the passage has a bore size adapted to deflect the regulator member cause an audible indication of a leak greater than a predetermined threshold.

Illustrative embodiments of methods for providing reduced pressure treatment are also described, including methods that store a charging pressure within a charging chamber, deliver a desired therapy pressure from a regulated chamber to a tissue site, reduce the pressure within the regulated chamber by allowing fluid communication between the charging chamber and the regulated chamber when a pressure within the regulated chamber exceeds the desired therapy pressure, and provide an audible indication of a leak.

Other objects, features, and advantages of the illustrative embodiments will become apparent with reference to the drawings and detailed description that follow.

DETAILED DESCRIPTION OF ILLUSTRATIVE EMBODIMENTS

Figure 1:
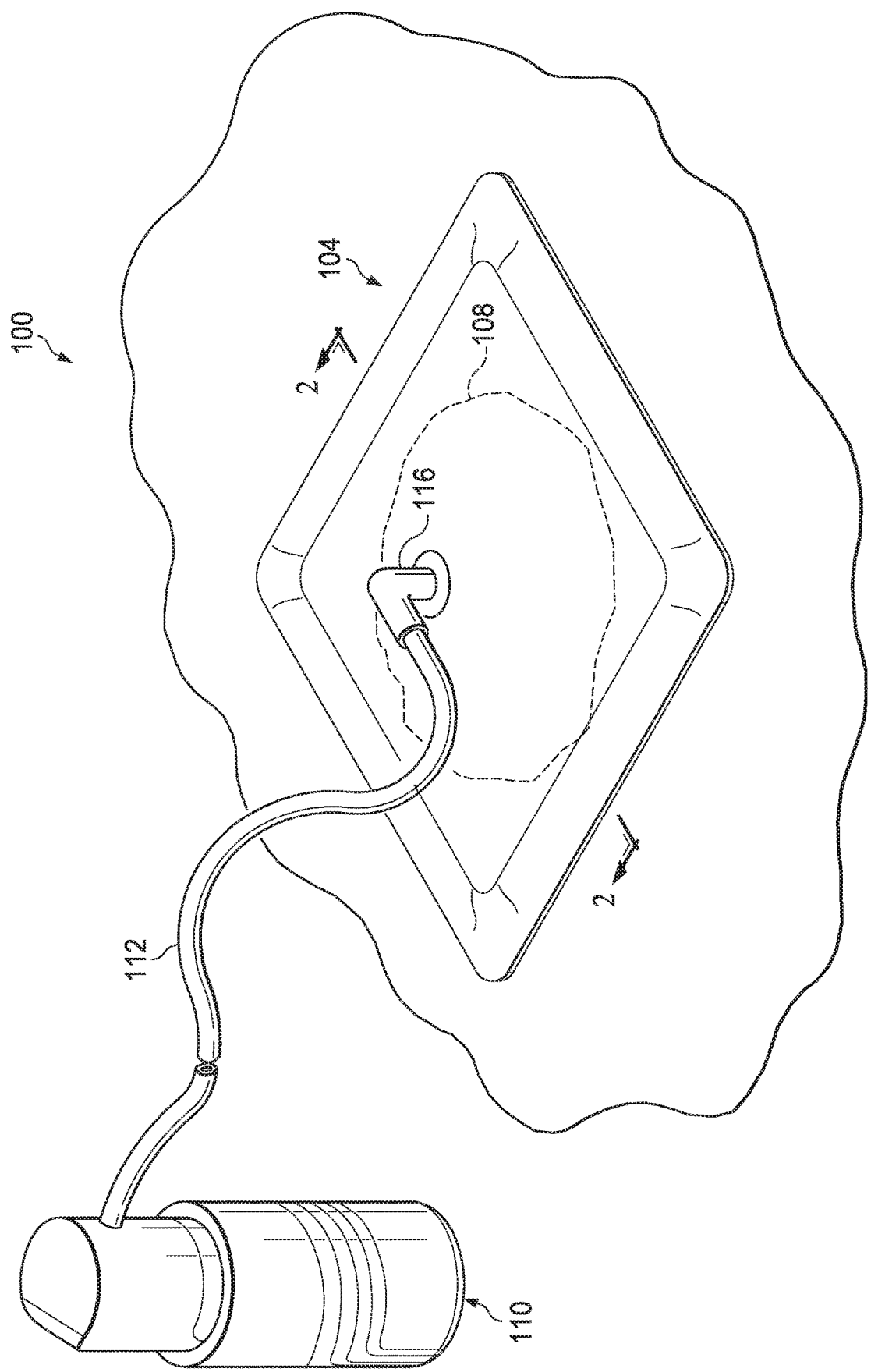
FIG. 1 illustrates a perspective view of a reduced pressure treatment system according to an illustrative embodiment, the reduced pressure treatment system having a reduced pressure pump adapted to deliver a reduced pressure to a dressing positioned at a tissue site.

New and useful systems, methods, and apparatuses associated with providing reduced-pressure therapy are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

In general, reduced-pressure therapy can be beneficial for wounds of all severity, but the cost and complexity of reduced-pressure therapy systems often limit the application of reduced-pressure therapy to large, highly-exudating wounds present on patients undergoing acute or chronic care, as well as other severe wounds that are not readily susceptible to healing without application of reduced pressure. For example, the complexity of conventional reduced-pressure therapy systems can limit the ability of a person with little or no specialized knowledge from administering reduced-pressure therapy. The size of many reduced-pressure therapy systems may also impair mobility. Many reduced-pressure therapy systems also require careful cleaning after each treatment, and may require electrical components or other powered devices to supply the reduced pressure for treatment.

Eliminating power requirements can increase mobility, and generally reduce cost, as well. For example, a manually-actuated or manually-charged pump can be used as a source of reduced pressure instead of an electrically-powered pump. However, leaks in a dressing can gradually erode energy stored in pump. Large leaks are also common when a dressing is first applied. A manually-actuated reduced-pressure therapy system can be particularly sensitive to leaks because the capacity of such a system to generate reduced pressure is typically more limited than electrically-powered pumps. The presence of a leak at a dressing can quickly dissipate the therapeutic pressure generated by a pump.

Figure 2:
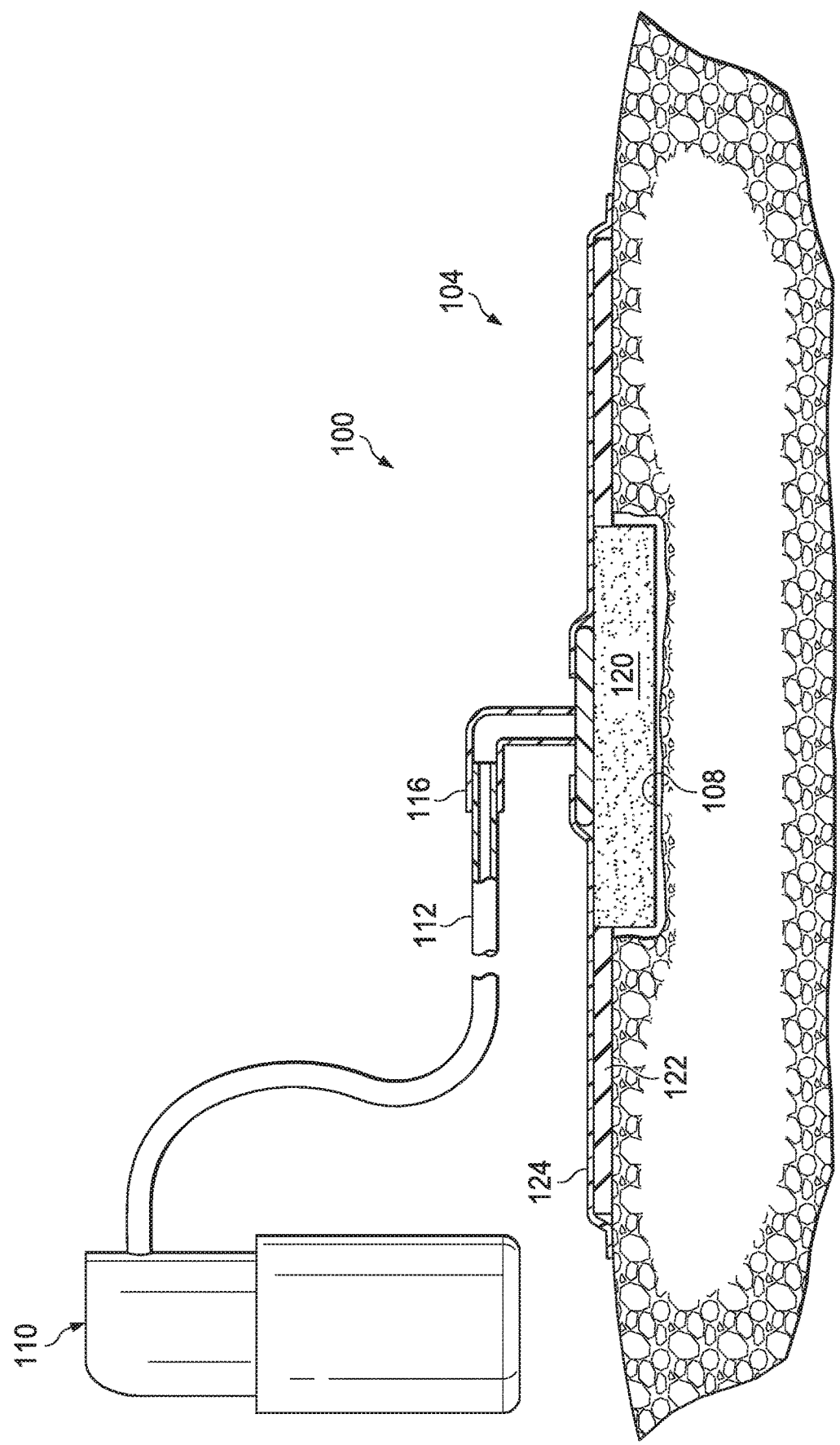
FIG. 2 depicts a cross-sectional front view of the dressing of FIG. 1 taken at 2-2.

As described herein, a reduced-pressure treatment system 100 can overcome these shortcomings and others by providing audible feedback of flow indicative of a leak. Referring to FIGS. 1 and 2, a reduced pressure treatment system 100 according to an illustrative embodiment includes a reduced pressure dressing 104 positioned at a tissue site 108 of a patient. The reduced pressure dressing 104 is fluidly connected to a reduced pressure source 110 by a conduit 112. The conduit 112 may fluidly communicate with the reduced pressure dressing 104 through a tubing adapter 116. In the embodiment illustrated in FIG. 1, the reduced pressure source 110 is a manually-actuated pump such as the regulated pressure pumps described herein. In another implementation, the reduced pressure source 110 may include pressure regulation capabilities but may initially be charged or re-charged to a selected reduced pressure by a reduced pressure or vacuum pump that is driven by an electric motor. In still another embodiment, the reduced pressure source 110 may be charged to the selected reduced pressure by a wall suction port such as are available in hospitals and other medical facilities.

The reduced pressure source 110 may be housed within or used in conjunction with a reduced pressure treatment unit (not shown), which may also contain sensors, processing units, alarm indicators, memory, databases, software, display units, and user interfaces that further facilitate the application of reduced pressure treatment to the tissue site 108. In one example, a sensor or switch (not shown) may be disposed at or near the reduced pressure source 110 to determine a source pressure generated by the reduced pressure source 110. The sensor may communicate with a processing unit that monitors and controls the reduced pressure that is delivered by the reduced pressure source 110. Delivery of reduced pressure to the reduced pressure dressing 104 and tissue site 108 encourages new tissue growth by maintaining drainage of exudate from the tissue site, increasing blood flow to tissues surrounding the tissue site, and creating microstrain at the tissue site.

The reduced pressure dressing 104 includes a distribution manifold 120 adapted to be positioned at the tissue site 108, and a seal layer 122 to seal the reduced pressure dressing 104 around the tissue site 108. A cover 124, or drape, is positioned over the distribution manifold 120 and the seal layer to maintain reduced pressure beneath the cover 124 at the tissue site. The cover 124 may extend beyond a perimeter of the tissue site and may include an adhesive or bonding agent on the cover 124 to secure the cover to tissue adjacent the tissue site. In one embodiment, the adhesive disposed on cover 124 may be used in lieu of the seal layer 122, however, the seal layer 122 may be used in conjunction with the adhesive of the cover 124 to improve sealing of the cover 124 at the tissue site 108. In another embodiment, the seal layer 122 may be used in lieu of adhesive disposed on cover 124.

The distribution manifold 120 of the reduced pressure dressing 104 is adapted to contact the tissue site 108. The distribution manifold 120 may be partially or fully in contact with the tissue site 108 being treated by the reduced pressure dressing 104. When the tissue site 108 is a wound, the distribution manifold 120 may partially or fully fill the wound.

The distribution manifold 120 may be any size, shape, or thickness depending on a variety of factors, such as the type of treatment being implemented or the nature and size of the tissue site 108. For example, the size and shape of the distribution manifold 120 may be customized by a user to cover a particular portion of the tissue site 108, or to fill or partially fill the tissue site 108. Although the distribution manifold 120 illustrated in FIG. 3 has a square shape, the distribution manifold 120 may be shaped as a circle, oval, polygon, an irregular shape, or any other shape.

In one illustrative embodiment, the distribution manifold 120 is a foam material that distributes reduced pressure to the tissue site 108 when the distribution manifold 120 is in contact with or near the tissue site 108. The foam material may be either hydrophobic or hydrophilic. In one non-limiting example, the distribution manifold 120 is an open-cell, reticulated polyurethane foam such as GranuFoam® dressing available from Kinetic Concepts, Inc. of San Antonio, Tex.

In the example in which the distribution manifold 120 is made from a hydrophilic material, the distribution manifold 120 also functions to wick fluid away from the tissue site 108, while continuing to provide reduced pressure to the tissue site 108 as a manifold. The wicking properties of the distribution manifold 120 draw fluid away from the tissue site 108 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The distribution manifold 120 may further promote granulation at the tissue site 108 when a reduced pressure is applied through the reduced pressure dressing 104. For example, any or all of the surfaces of the distribution manifold 120 may have an uneven, coarse, or jagged profile that causes microstrains and stresses at the tissue site 108 when reduced pressure is applied through the distribution manifold 120. These microstrains and stresses have been shown to increase new tissue growth.

In one embodiment, the distribution manifold 120 may be constructed from bioresorbable materials that do not have to be removed from a patient's body following use of the reduced pressure dressing 104. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 120 may further serve as a scaffold for new cell-growth, or a scaffold material may be used in conjunction with the distribution manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 3:
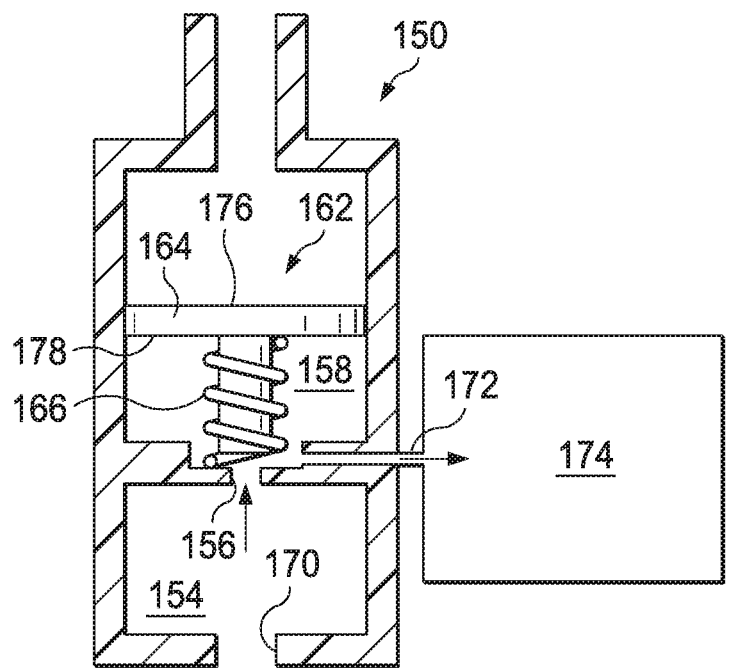
FIG. 3 illustrates a schematic of a reduced pressure treatment apparatus according to an illustrative embodiment, the reduced pressure treatment apparatus having a charging chamber, a regulated chamber, and a regulator member, the regulator member being shown in an open position.
Figure 4:
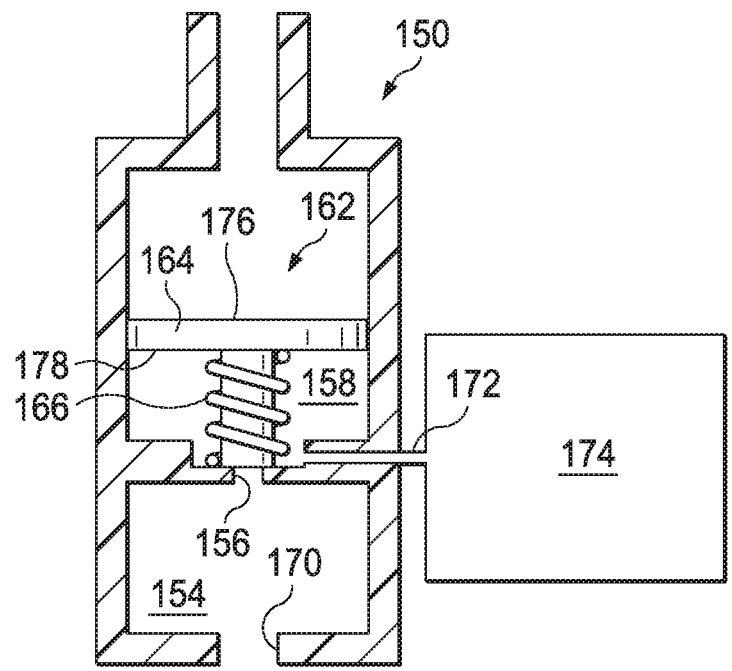
FIG. 4 depicts a schematic of the reduced pressure treatment apparatus of FIG. 3, the regulator member being shown in a closed position.

Referring to FIGS. 3 and 4, a reduced pressure treatment apparatus 150, or reduced pressure pump, or reduced pressure source, is schematically illustrated and includes a charging chamber 154 fluidly connected by a passage 156, or conduit, to a regulated chamber 158. A regulator member 162 is operably associated with the passage 156 to selectively allow or prevent fluid communication between the charging chamber 154 and the regulated chamber 158. In the embodiment illustrated in FIGS. 3 and 4, the regulator member 162 includes a piston 164 that is disposed within the regulated chamber 158. The regulator member 162 further includes a regulator spring 166 to bias the piston 164 toward an open position as illustrated in FIG. 3. In the open position, the piston 164 allows fluid communication through the passage 156. In a closed position (shown in FIG. 4), the piston 164 prevents or at least substantially reduces fluid communication through the passage 156.

As previously noted, the charging chamber 154 is fluidly connected to the regulated chamber 158 by passage 156. The charging chamber 154 may include an inlet 170 for introduction of a reduced pressure to the charging chamber 154, or as explained below, the charging chamber 154 may by operably associated with a piston-driven or other device to charge the charging chamber 154 with the reduced pressure. The charging chamber 154 is well suited to receive the reduced pressure from a device that is manually-actuated, or alternatively that is powered by electrical or other means.

The regulated chamber 158 is fluidly connected by a conduit 172 to a dressing 174. In one embodiment, the conduit 172 and dressing 174 may be similar to conduit 112 and dressing 104. When reduced pressure treatment is applied to the dressing 174 and a tissue site, it is desired to deliver a reduced pressure to dressing 174 that is about equal to a desired therapy pressure. To accomplish this, the charging chamber 154 stores a first pressure that is less than an ambient pressure. The regulated chamber 158 stores a second pressure that is also less than the ambient pressure. The first pressure stored in the charging chamber 154 is less than the second pressure stored in the regulated chamber 158.

When the second pressure is less than or equal to the desired therapy pressure, a counteracting force on the piston is able to overcome a biasing force exerted by the regulator spring 166 on the piston 164. The counteracting force on the piston is a result of a pressure differential across opposite sides of the piston 164. On a first side 176 of the piston 164, the ambient pressure (e.g. atmospheric pressure) surrounding the reduced pressure treatment apparatus 150 acts on the piston 164. On a second side 178 of the piston 164, the second pressure within the regulated chamber 158 acts on the piston. Since the second pressure is less than the ambient pressure, the counteracting force acts on the first side 176 of the piston 164 against the biasing force of the regulator spring 166. When the second pressure in the regulated chamber 158 is less than or equal to the desired therapy pressure, the piston 164 moves to and remains in the closed position.

If the second pressure in the regulated chamber 158 rises above (i.e. exceeds) the desired therapy pressure, possibly due to fluid leaks at the dressing 174 or within the reduced pressure treatment apparatus 150, the piston 164 is biased back to the open position by the regulator spring 166. In the open position, fluid communication is allowed between the charging chamber 154 and the regulated chamber 158. Since the first pressure in the charging chamber 154 is less than the second pressure in the regulated chamber 158, the second pressure in the regulated chamber 158 drops until the desired therapy pressure is reached, at which point the piston 164 again moves to the closed position. In one embodiment, the first pressure stored in the charging chamber 154 is about −150 mm Hg, and the desired therapy pressure is about −125 mm Hg.

If a dressing has a small leak, regulator member 162 can maintain the therapy pressure. However, regulator member 162 may not be able to maintain the therapy pressure if a leak exceeds a certain tolerance, which is dependent upon the size of the restrictions on the entry and exit sides of the regulated chamber 158. For example, passage 156 and conduit 172 may be sized such that a leak exceeding a threshold causes regulator member 162 to remain partially open with a gap between regulator member 162 and passage 156 that allows a steady flow of air through passage 156 and conduit 172. Moreover, the sizes of passage 156 and conduit 172 may be calibrated such that the flow of air through the gap causes an audible note, alerting an operator of an unexpected loss of therapeutic pressure.

Figure 5:
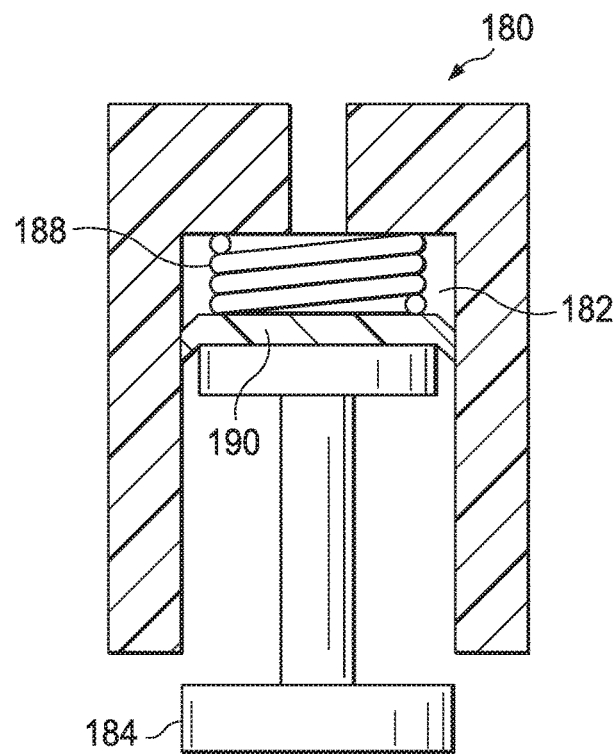
FIG. 5 illustrates a schematic of a piston-driven device for use with the reduced pressure treatment apparatus of FIG. 3 to charge the charging chamber with a reduced pressure, the piston-driven device having a piston shown in a compressed position.
Figure 6:
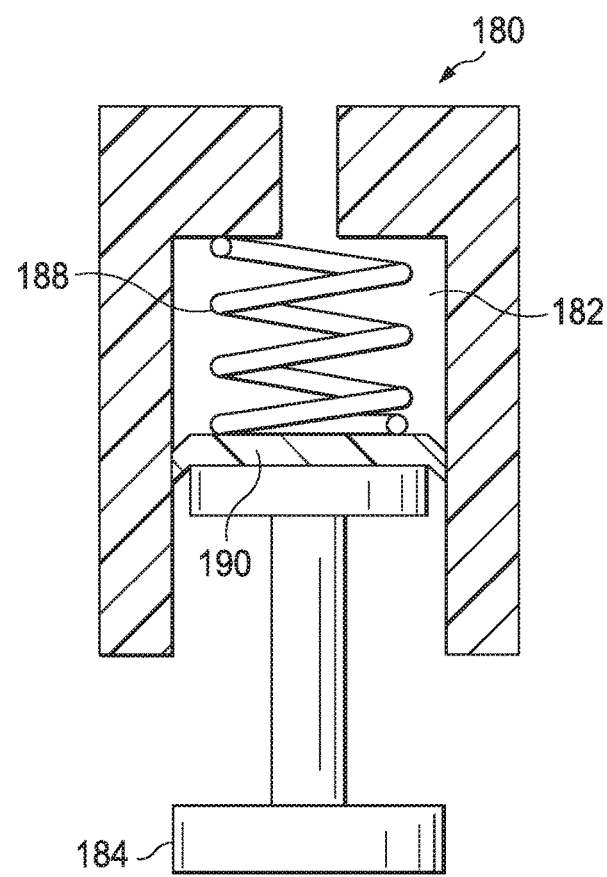
FIG. 6 depicts a schematic of the piston-driven device of FIG. 5 with the piston shown in an extended position.

Referring to FIGS. 5 and 6, a piston-driven device 180 is provided for charging a charging chamber 182 similar to charging chamber 154. The piston-driven device 180 includes a piston 184 disposed within the charging chamber 182. This piston 184 is capable of reciprocal movement between a compressed position (see FIG. 5) and an extended position (see. FIG. 6). A piston spring 188 or other biasing member is operably associated within the piston 184 to bias the piston 184 toward the extended position.

To charge the charging chamber 182, the piston 184 is moved to the compressed position. A seal 190 or other valve member allows fluid within the charging chamber 182 to exit the charging chamber 182 as a volume of the charging chamber 182 decreases. After moving the piston 184 to the compressed position, the piston spring 188 attempts to return the piston 184 to the extended position. As the volume of the charging chamber 182 increases, the seal 190 prevents fluid from entering the charging chamber 182 past the seal 190, which results in a pressure drop within the charging chamber 182. After the piston 184 has moved completely to the extended position, the piston 184 may be moved again to the compressed position to recharge the charging chamber 182 with a reduced pressure.

The piston-driven device 180 may be manually-actuated by a user compressing the piston 184. Alternatively, the piston 184 may be actuated by an electrical, hydraulic, or pneumatic actuator. For all of the charging chambers described herein, it should be noted that reduced pressure may be supplied to the charging chamber by manual or electrically powered means.

Figure 7:
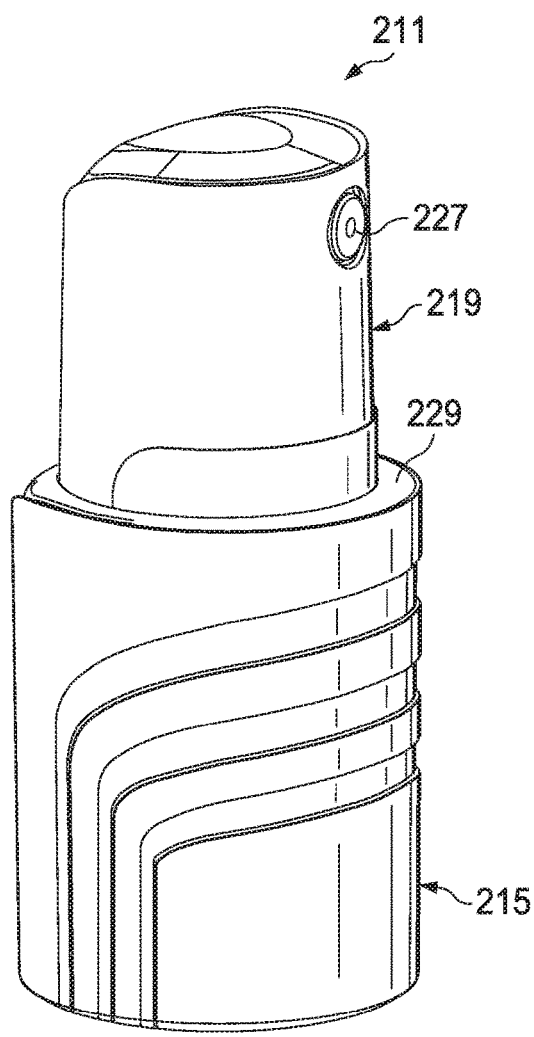
FIG. 7 illustrates a side perspective view of a reduced pressure treatment apparatus according to an illustrative embodiment.
Figure 8:
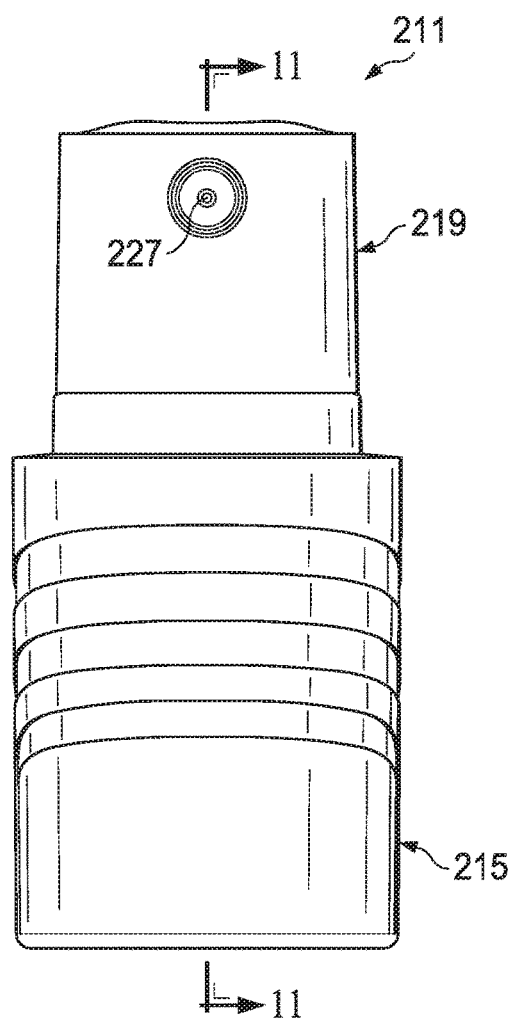
FIG. 8 depicts a front view of the reduced pressure treatment apparatus of FIG. 7.

Referring to FIGS. 7 and 8, a reduced pressure treatment apparatus, or reduced pressure source 211 according to an illustrative embodiment is a manually-actuated pump having a first, or outer barrel 215 and a second, or inner barrel 219. The first barrel 215 includes a passage 223 (see FIG. 9) having a closed end and an open end. The passage 223 may be defined by a substantially cylindrical wall. The passage 223 slidingly receives the second barrel 219 through the open end of the first barrel 215, and the second barrel 219 is movable between an extended position and a compressed position. While the first and second barrels are illustrated as having substantially cylindrical shapes, the shapes of the barrels could be any other shape that permits operation of the device.

In the extended position, the reduced pressure source 211 is discharged and does not actively deliver or supply a reduced pressure. In the compressed position, the reduced pressure source 211 is primed or charged, and the reduced pressure source 211 is capable of delivering a reduced pressure. An outlet port 227 is provided on the second barrel 219 and is adapted for fluid communication with a delivery tube or other conduit, which may be similar to delivery tube 135, such that reduced pressure generated by the reduced pressure source 211 may be delivered to the tissue site.

Figure 9:
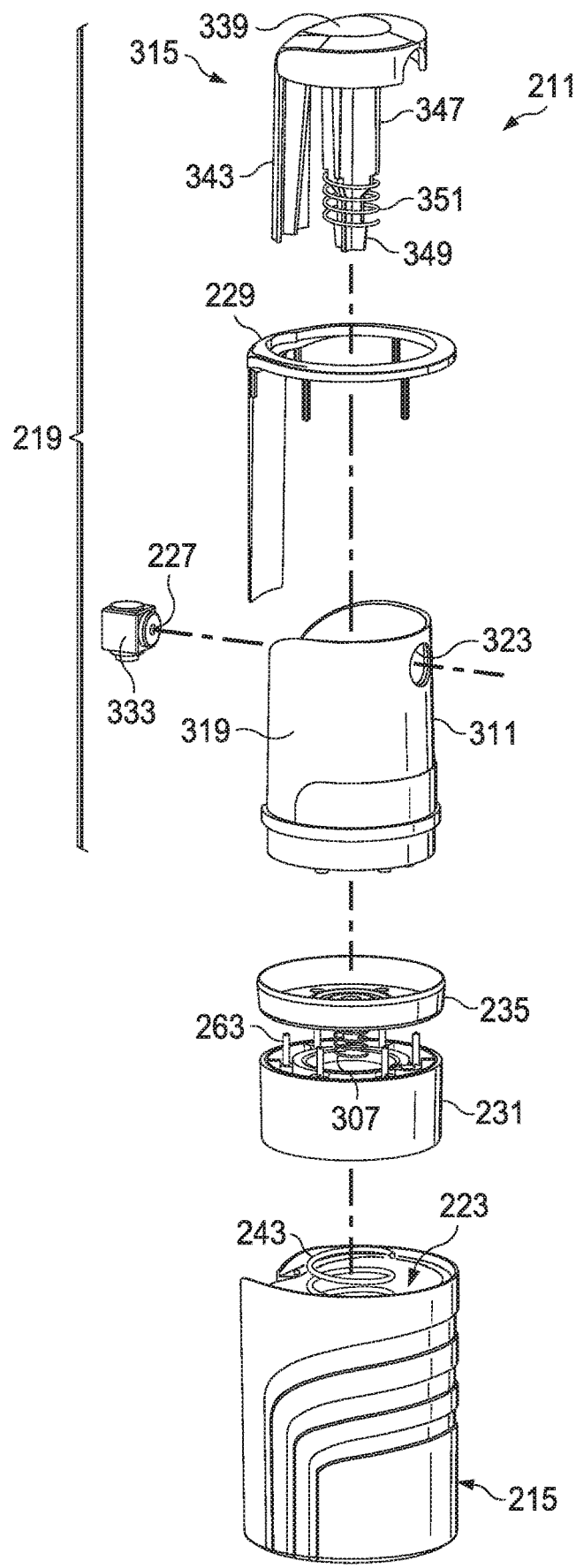
FIG. 9 illustrates an exploded side perspective view of the reduced pressure treatment apparatus of FIG. 7.
Figure 10:
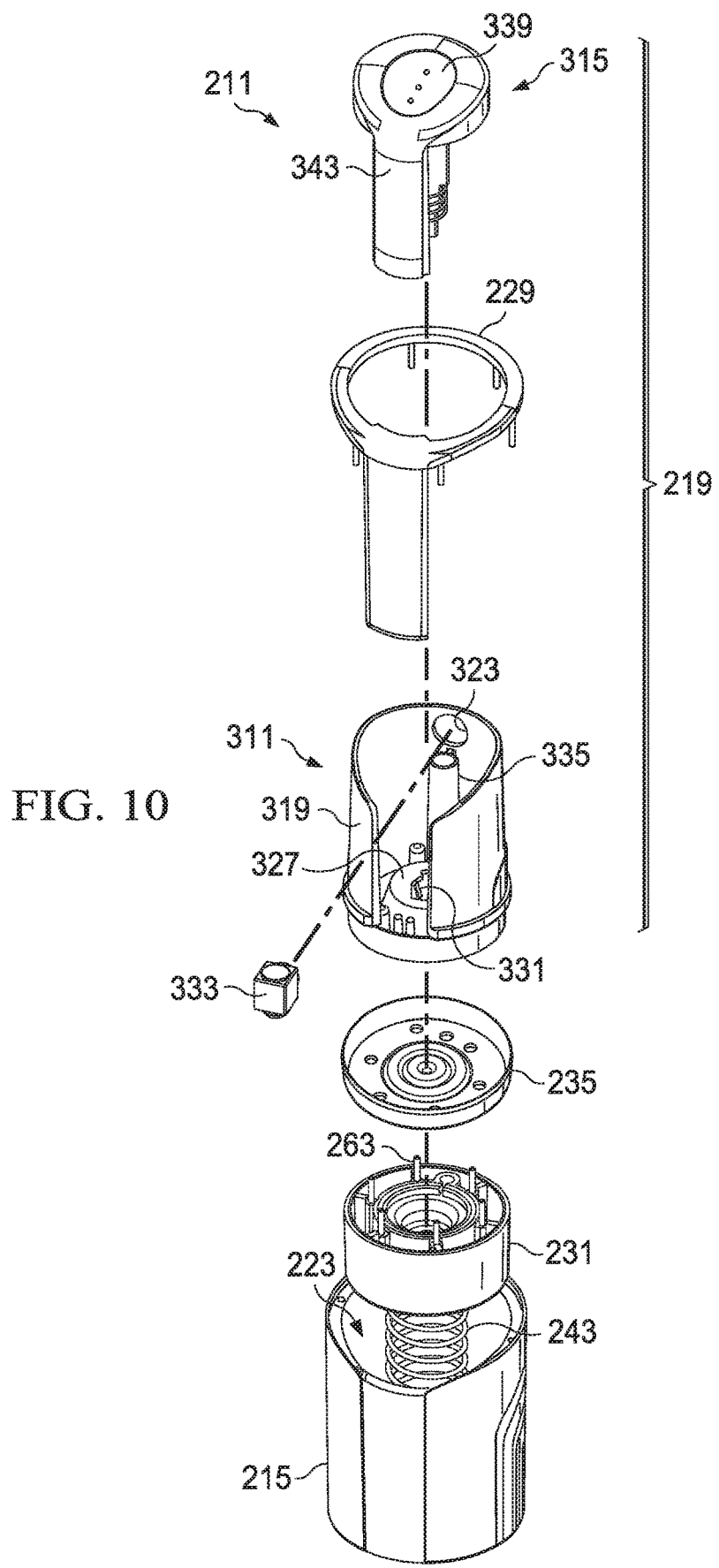
FIG. 10 depicts an exploded rear perspective view of the reduced pressure treatment apparatus of FIG. 7.
Figure 11:
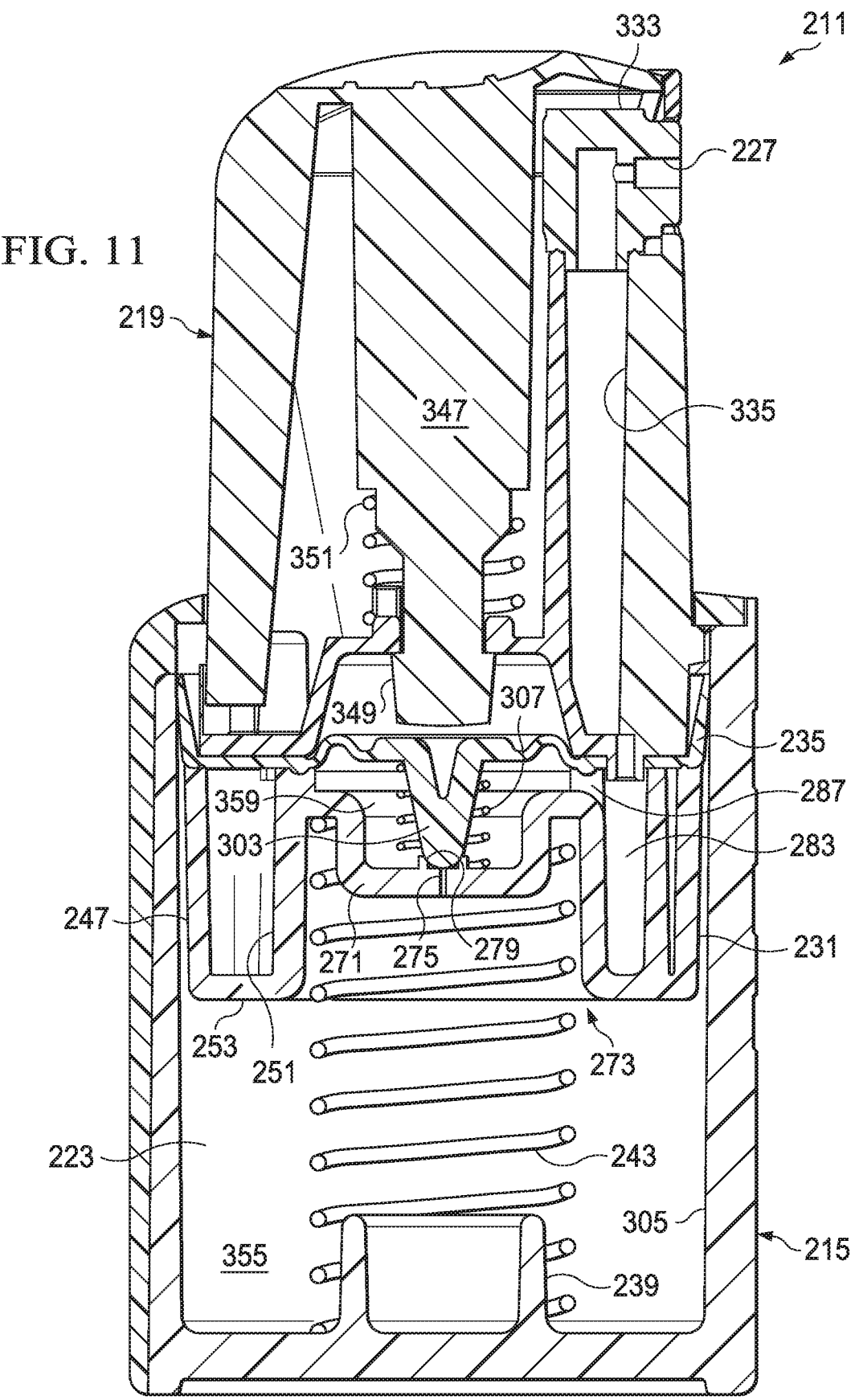
FIG. 11 illustrates a cross-sectional side view of the reduced pressure treatment apparatus of FIG. 8 taken at 11-11, the reduced pressure treatment apparatus shown in an extended position.

Referring to FIGS. 9-11, the reduced pressure source 211 further includes a barrel ring 229, a piston 231, and a seal 235. The barrel ring 229 is positioned at the open end of the first barrel 215 to circumscribe the second barrel 219. The barrel ring 229 eliminates large gaps between the first barrel 215 and the second barrel 219 at the open end of the first barrel 215. When the reduced pressure source 211 is assembled, the piston 231 and seal 235 are slidingly received within the passage 223 of the first barrel 215. Both the piston 231 and the seal 235 are positioned in the passage 223 between the second barrel 219 and the closed end of the first barrel 215, the seal 235 being positioned between the second barrel 219 and the piston 231.

Referring more specifically to FIG. 11, the first barrel 215 includes a protrusion 239 extending from the closed end of the first barrel 215 into the passage 223. A piston spring 243 or other biasing member is positioned within the passage 223 and is received at one end of the piston spring 243 by the protrusion 239. The protrusion 239 reduces lateral movement of the piston spring 243 within the passage 223. An opposite end of the piston spring 243 is received against the piston 231. The piston spring 243 biases the piston 231, the seal 235, and the second barrel 219 toward the extended position.

Figure 12:
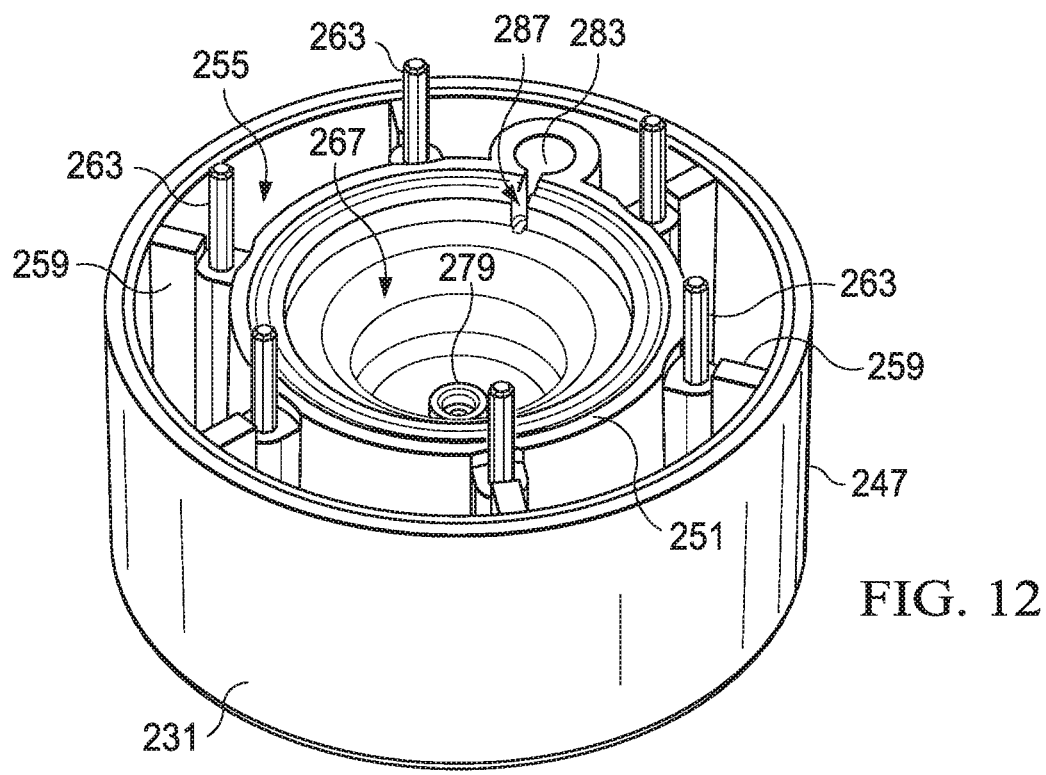
FIG. 12 depicts a top-rear perspective view of a piston of the reduced pressure treatment apparatus of FIG. 7.
Figure 13:
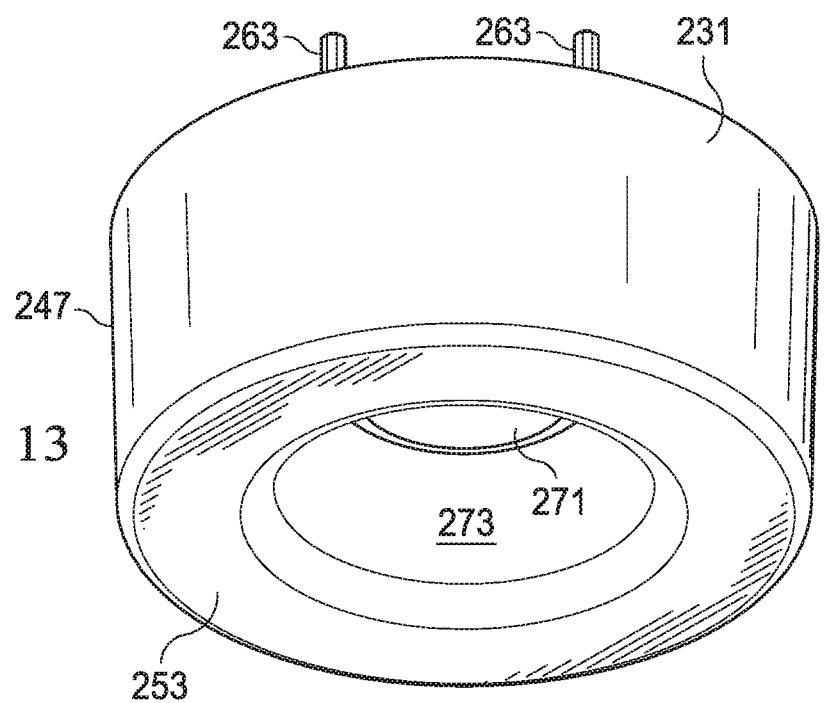
FIG. 13 illustrates a bottom-rear perspective view of the piston of FIG. 12.

Referring again to FIGS. 9-11, but also to FIGS. 12 and 13, the piston 231 includes an outer wall 247 and an inner wall 251 joined by an outer floor 253. An annulus 255 is defined between the outer wall 247 and the inner wall 251, and a plurality of radial supports 259 are positioned between the outer wall 247 and the inner wall 251 in the annulus 255. The radial supports 259 provide additional rigidity to the piston 231, yet the presence of the annulus 255 as well as the sizes and spacing of the radial supports 259 within the annulus 255 reduces the weight of the piston 231 as compared to a single-wall piston that includes no annulus. However, it should be apparent that either piston design would be suitable for the reduced pressure source described herein.

A plurality of guides 263 is disposed on the piston 231, and in one embodiment, one of the guides 263 is disposed on each radial support 259. As described in more detail herein, the guides 263 serve to align the piston 231 relative to the seal 235 and the second barrel 219. The guides 263 further serve to secure the piston 231 to the second barrel 219 by means of a friction fit.

The piston 231 further includes an inner bowl 267 that is defined by the inner wall 251 and an inner floor 271. In one embodiment, the inner floor 271 may be two-tiered or multi-tiered as illustrated in FIG. 11, but the inner floor 271 may instead be single-tiered and/or substantially planar. The inner floor 271 may be positioned such that a recess 273 is defined beneath the inner floor 271 to receive an end of the piston spring 243 (see FIGS. 11 and 13). A regulator passage 275 passes through the inner floor 271. A valve seat 279 may be positioned in the inner bowl 267 near the regulator passage 275 such that fluid communication through the regulator passage 275 may be selectively controlled by selective engagement of the valve seat 279 with a valve body (described in more detail with reference to FIG. 15).

A well 283 is positioned in the annulus 255 of the piston 231, and a channel 287 is fluidly connected between the well 283 and the inner bowl 267. The channel 287 allows fluid communication between the well 283 and the inner bowl 267.

Figure 14:
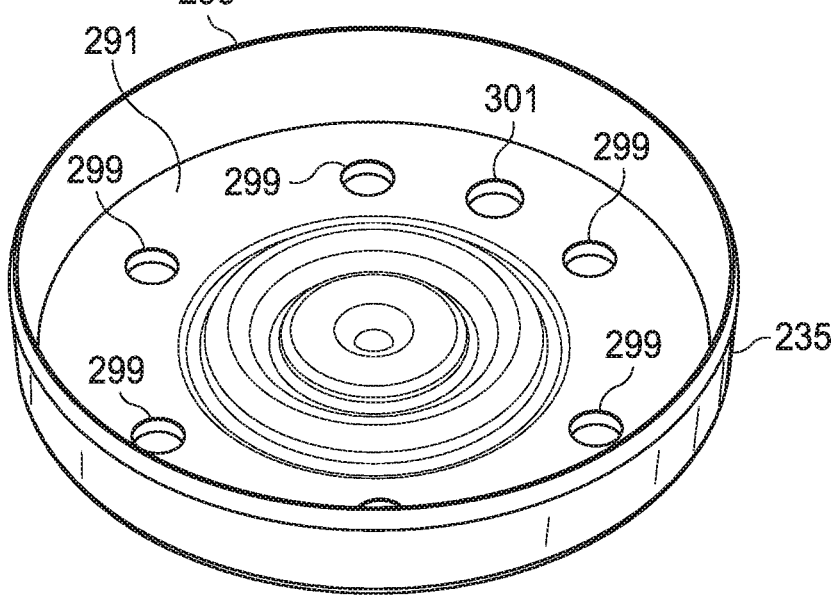
FIG. 14 depicts a top-rear perspective view of a seal of the reduced pressure treatment apparatus of FIG. 7.
Figure 15:
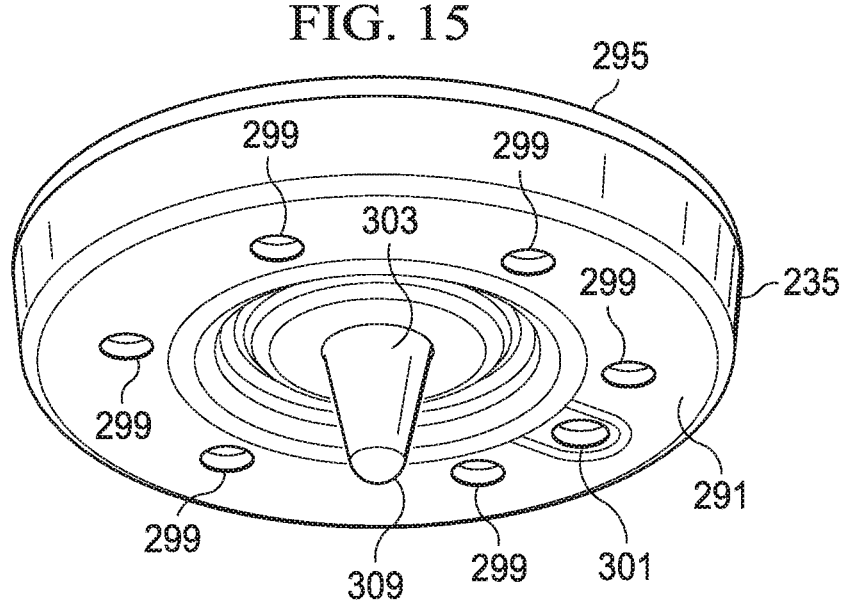
FIG. 15 illustrates a bottom-rear perspective view of the seal of FIG. 14.

Referring still to FIGS. 9-11, but also to FIGS. 14 and 15, the seal 235 includes a central portion 291 that is circumscribed by a skirt portion 295. A plurality of guidance apertures 299 are disposed in the central portion 291 to receive the guides 263 of the piston 231 when the reduced pressure source 211 is assembled. A communication aperture 301 is similarly disposed in the central portion 291, and in one embodiment, the communication aperture 301 is radially spaced an equal distance from a center of the seal as the guidance apertures 299. The communication aperture 301 permits fluid communication through the central portion 291 of the seal 235 and with the well 283 of the piston 231 upon assembly.

The skirt portion 295 of the seal 235 extends axially and radially outward from the central portion 291. As illustrated in FIG. 11, the radially-outward-extending skirt portion 295 engages an inner surface 305 of the first barrel 215 to permit unidirectional fluid communication past the seal 235. In other words, the skirt portion 295 of the seal 235 allows fluid to flow past the skirt portion 295 when the fluid flow is directed from the side of the seal 235 on which the piston 231 is disposed toward the opposite side of the seal 235. The skirt portion 295, however, substantially prevents fluid flow in the opposite direction. While the skirt portion of the seal effectively controls fluid communication past the skirt portion 295, a valve member such as, for example, a check valve or other valve could instead be used to perform this function.

As illustrated in more detail in FIGS. 11 and 15, a valve body 303 is positioned on the central portion 291 of the seal 235. Although valve bodies of many types, shapes and sizes may be used, the valve body 303 may be cone-shaped with an apex 309 that is adapted to sealingly engage the valve seat 279 of the piston 231. While the valve body 303 is illustrated as being an integral part of the seal 235, the valve body 303 may alternatively be a separate component from the seal 235 that is provided to engage the valve seat 279.

In one embodiment, both the seal 235 and the valve body 303 are made from an elastomeric material, which could include without limitation a medical grade silicone. While many different materials may be used to construct, form, or otherwise create the seal 235 and valve body 303, it is preferred that a flexible material be used to improve the sealing properties of the skirt portion 295 with the inner surface 305 and the valve body 303 with the valve seat 279.

Figure 20:
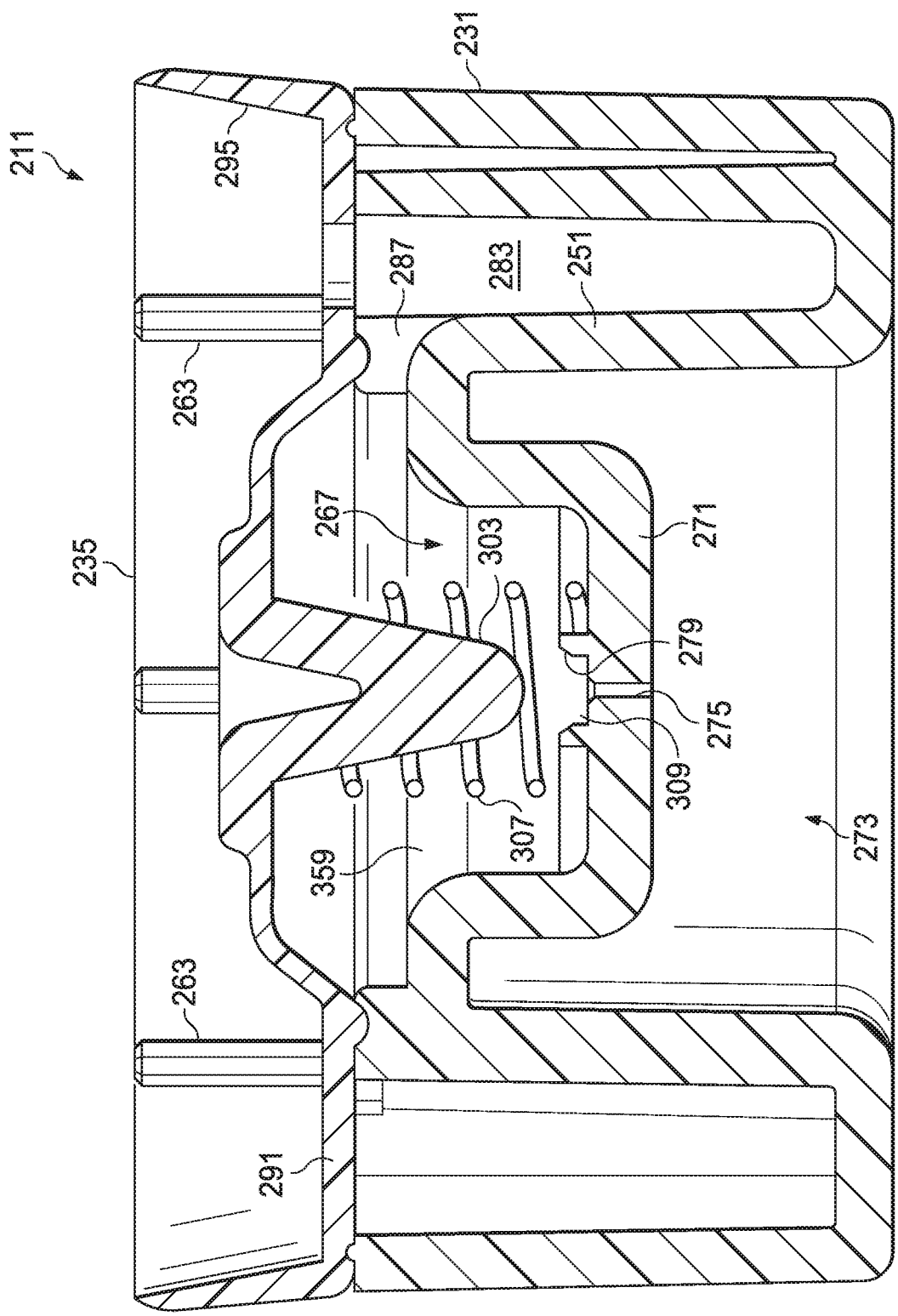
FIG. 20 depicts an enlarged cross-sectional view of the reduced pressure treatment apparatus of FIG. 19 with the valve body shown in an open position.
Figure 20A:
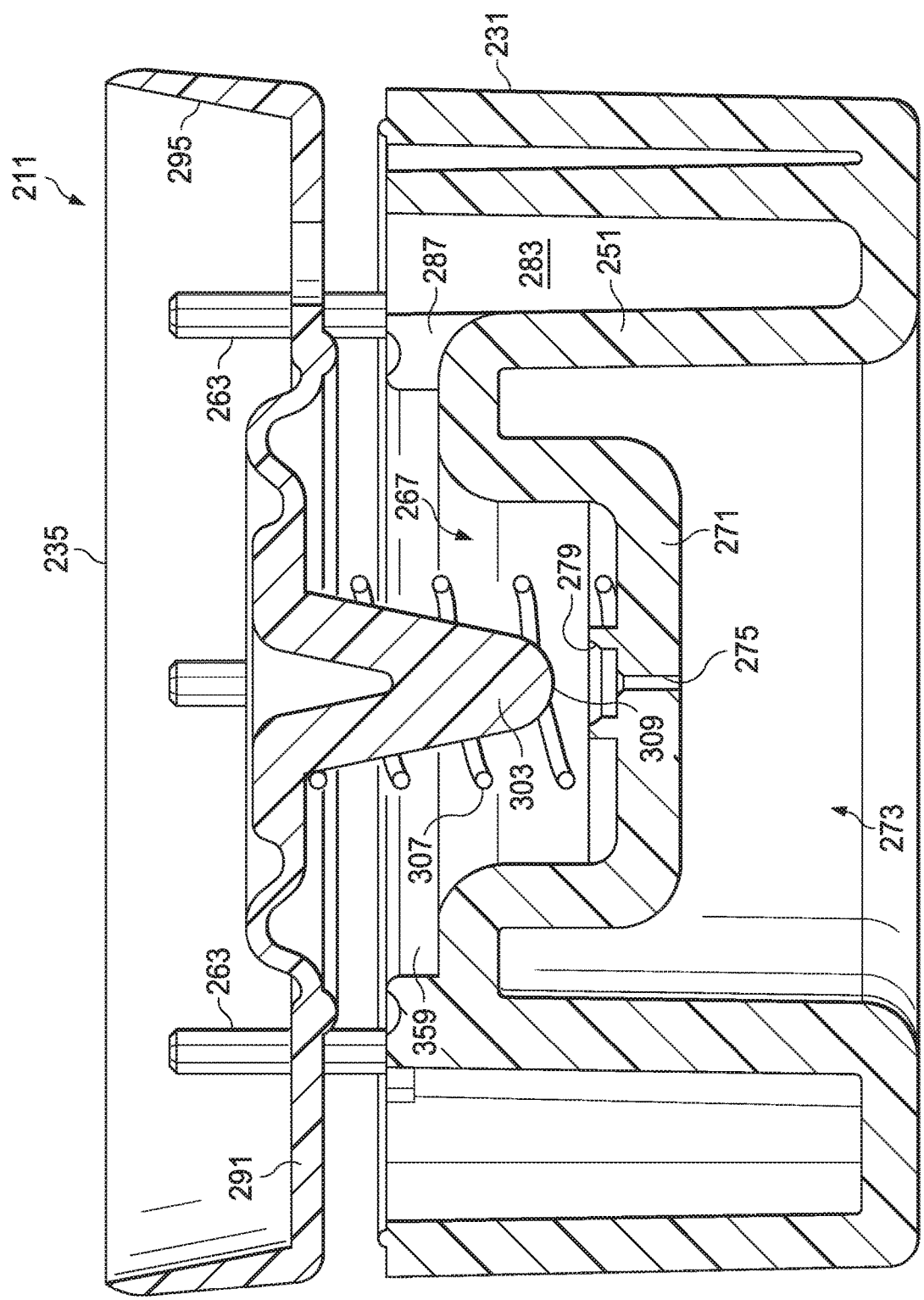
FIG. 20A depicts an enlarged cross-sectional view, similar to that of FIG. 20, of a reduced pressure treatment apparatus according to an illustrative embodiment.

Referring more specifically to FIG. 11, a regulator spring 307 is provided to bias the valve body 303 away from the piston 231 and the valve seat 279. One end of the regulator spring 307 may be positioned concentrically around the valve seat 279 within the inner bowl 267 of the piston 231, while another end of the regulator spring 307 may be positioned around the valve body 303. The biasing force provided by the regulator spring 307 urges the valve body 303 toward an open position in which fluid communication is permitted through the regulator passage 275. In one embodiment, when the spring 307 biases the valve body 303 toward the open position, only the central portion 291 of the seal 235 moves upward due to the flexibility of the seal (see FIG. 20). In another embodiment, the biasing force of the spring 307 may move the entire seal 235 toward the open position as illustrated in FIG. 20A.

Figure 16:
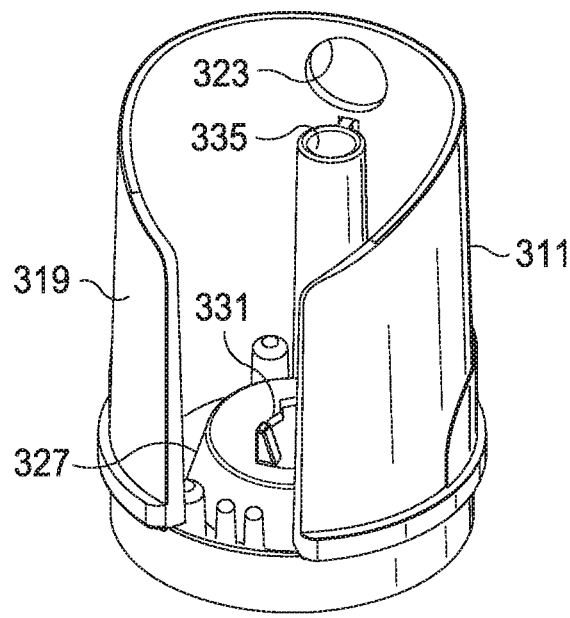
FIG. 16 depicts a top-rear perspective view of a second barrel of the reduced pressure treatment apparatus of FIG. 7.
Figure 17:
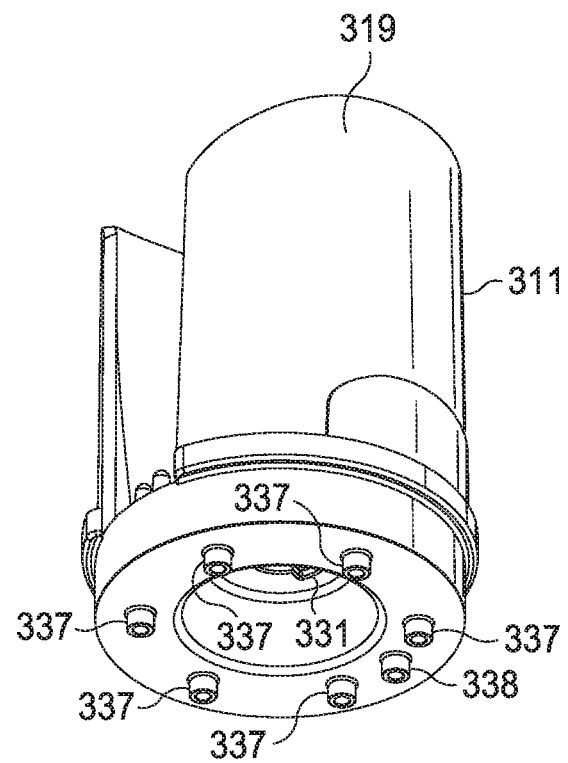
FIG. 17 illustrates a bottom-rear perspective view of the second barrel of FIG. 16.

Referring again to FIGS. 9-11, but also to FIGS. 16 and 17, the second barrel 219 includes a first housing portion 311 and a second housing portion 315. The first housing portion 311 includes an outer shell 319 having an aperture 323 disposed near an open end of the first housing portion 311. A floor 327 is integrally formed with or otherwise connected to the outer shell 319 on an end of the first housing portion 311 opposite the open end. A passage 331 may be centrally disposed in the floor 327. A boss 333 is integrated with or connected to the first housing portion 311. The boss 333 includes the outlet port 227, which is physically aligned with the aperture 323 to allow a delivery tube to be fluidly connected to the outlet port 227. In one embodiment, the boss 323 is a ninety degree fluid fitting that permits the outlet port 227 to fluidly communicate with a conduit 335 positioned within the first housing portion 311. The conduit 335 may be a rigid conduit that is formed from the same or similar material to that of the outer shell, or in one alternative embodiment, the conduit 335 may be flexible.

Referring more specifically to FIG. 17, a plurality of guidance apertures 337 are disposed in the floor 327 of the first housing portion 311. When the reduced pressure source 211 is assembled, the guidance apertures 337 receive the guides 263 of the piston 231 to ensure that the second barrel 219 remains aligned with the piston 231. A friction fit between the guides 263 and guidance apertures 337 assist in securing the relative positions of the piston 231 and the second barrel 219. It should be readily apparent, however, that the piston 231 and the second barrel 219 may be secured by alternative means. A communication aperture 338 is also disposed in the floor 327 to allow fluid communication with the conduit 335 through the floor 327.

The second housing portion 315 may include an end cap 339 integrally or otherwise connected to a guide 343. Together, the end cap 339 and guide 343 slidingly engage the outer shell 319 of the first housing portion 311 to create a substantially closed second barrel 219 (with the exception of various apertures and passages). While the second barrel 219 may be constructed from fewer components, the existence of the first housing portion 311 and the second housing portion 315 allows easier access within the second barrel 219 and also allows easier assembly of the reduced pressure source 211. Additional advantages regarding the sliding engagement of the first housing portion 311 and the second housing portion 315 are explained in more detail below.

A shaft 347 extends from the end cap 339 and includes an engagement end 349 opposite the end cap 339. When the second barrel 219 is assembled, the shaft may be substantially coaxial to a longitudinal axis of the second barrel 219 and extend through the passage 331 in the floor 327 of the first housing portion 311. A spring 351 is positioned within the second barrel 219 such that one end of the spring 351 bears upon the floor 327 of the first housing portion 311 and another end of the spring 351 bears upon the shaft 347 or another portion of the second housing portion 315. The spring 351 biases the shaft 347 and other portions of the second housing portion 315 toward a disengaged position (see position of shaft 347 in FIG. 11) in which the engagement end 349 of the shaft 347 does not bear upon the seal 235 or valve body 303. The sliding relationship and engagement between the first and second housing portions 311, 315 allows a user to exert a force on the second housing portion (against the biasing force of the spring 351) to move the second housing portion 315 to an engaged position. In the engaged position, the engagement end 345 of the shaft 347 bears upon the seal 235 above the valve body 303 (see FIG. 18), which forces the valve body 303 against the valve seat 279, thereby preventing fluid communication through the regulator passage 275.

When the reduced pressure source 211 is assembled, as illustrated in FIG. 11, a charging chamber 355 is defined within the first barrel 215 beneath the piston 231. A regulated chamber 359 is defined within the inner bowl 267 of the piston 231 beneath the seal 235. The regulator passage 275 allows selective fluid communication between the charging chamber 355 and the regulated chamber 359 depending on the position of the valve body 303. The regulated chamber 359 fluidly communicates with the well 283 of the piston 231 through the channel 287. The well 283 is aligned with the communication aperture 301 of the seal 235 and the communication aperture 338 of the first housing portion 311, which allows fluid communication between the well 283 and the conduit 335 and outlet port 227 of the second barrel 219.

While the regulator passage 275 is illustrated as being disposed within the piston 231, the regulator passage 275 could instead be routed through the wall of the first barrel 215. The regulator passage 275 could be any conduit that is suitable for allowing fluid communication between the chambers.

In operation, the reduced pressure source 211 is capable of being used with other components of a reduced pressure treatment system similar to those of reduced pressure treatment system 100 (see FIG. 1). The outlet port 227 of the reduced pressure source 211 is adapted to be connected to a delivery tube or other conduit that is fluidly connected to a tissue site. Although a fluid canister could be integrated into the reduced pressure source 211, in one embodiment, the reduced pressure source 211 is not intended to collect wound exudates or other fluids within any internal chamber. In one embodiment, the reduced pressure source 211 may either be used with low-exudating wounds, or an alternative collection system such as an external canister or absorptive dressing may be used to collect fluids.

Figure 18:
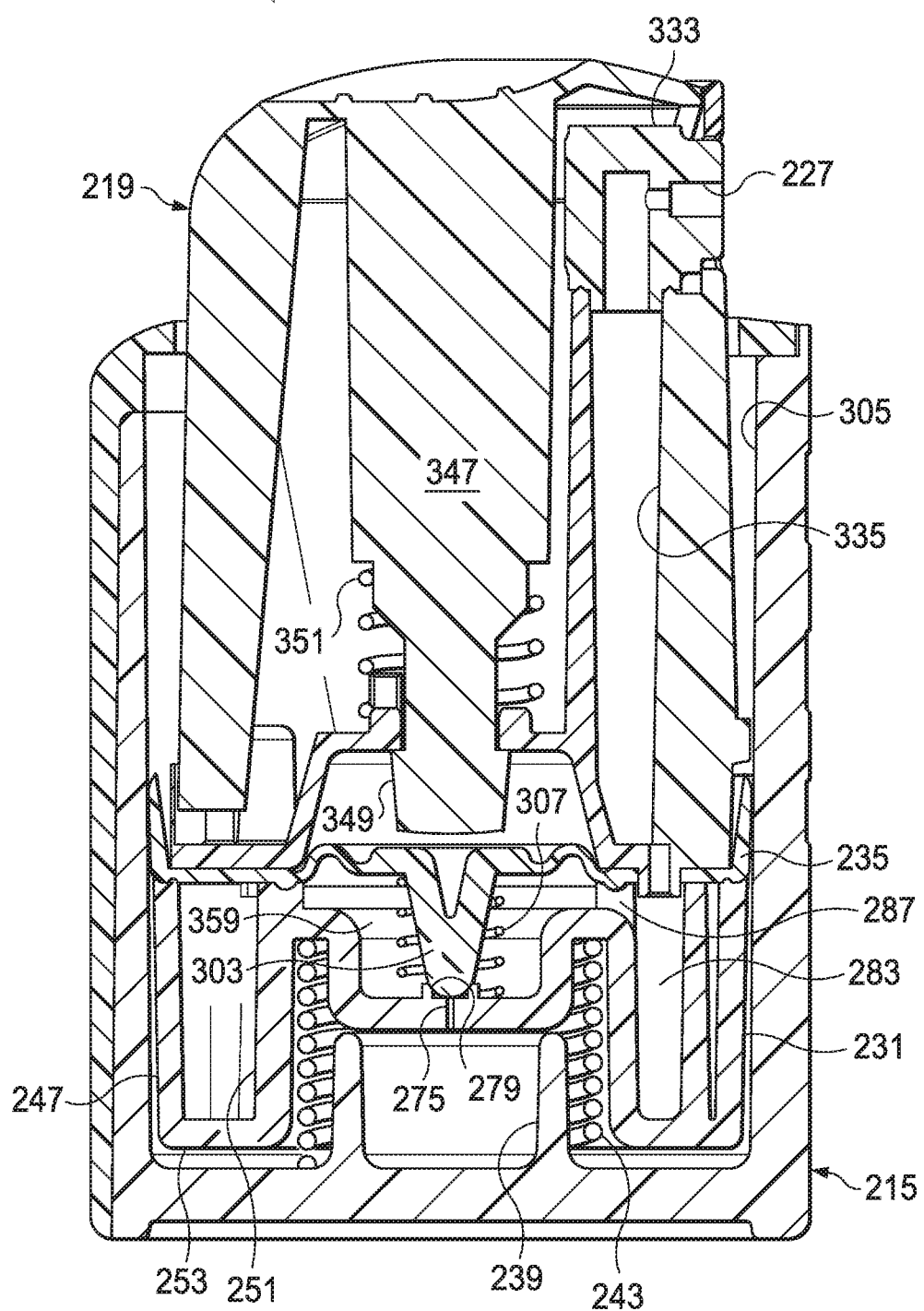
FIG. 18 depicts a cross-sectional side view of the reduced pressure treatment apparatus of FIG. 7, the reduced pressure treatment apparatus shown in a compressed position.

Referring to FIGS. 11 and 18, the extended position (see FIG. 11) and the compressed position (see FIG. 18) of the reduced pressure source 211 are illustrated. In the extended position, the reduced pressure source 211 is not "charged" and is thus not capable of delivering reduced pressure to the outlet port 227. To prime the reduced pressure source 211, the second barrel 219 is manually compressed into the first barrel 215 by a user such that the reduced pressure source 211 is placed in the compressed position. The force exerted by the user on the second barrel 219 must be greater than the biasing force provided by the piston spring 243. As the second barrel 219 compresses within the first barrel 215 and moves toward the closed end of the first barrel 215, the force being exerted on the second barrel 219 by the user is also transmitted to the seal 235 and piston 231. The movement of the second barrel 219, the seal 235, and the piston 231 into the compressed position decreases the volume of the charging chamber 355. As the volume of the charging chamber 355 decreases, the pressure in the charging chamber 355 increases, but air and other gases within the charging chamber 355 are allowed to escape past the skirt portion 295 of the seal 235 due to the increased pressure within the charging chamber 355.

When the user releases the compressive force exerted upon the second barrel 219, the biasing force exerted by the piston spring 243 on the piston 231 moves the piston 231, the seal 235, and the second barrel 219 toward the extended position. As this movement occurs, the volume of the charging chamber 355 increases. Since the skirt portion 295 of the seal 235 allows only unidirectional flow, air and other gases are not permitted to enter the charging chamber 355 past the skirt portion 295. A resulting drop in pressure (i.e., a generation of reduced pressure) occurs within the charging chamber 355 as the volume increases. The amount of reduced pressure generated within the charging chamber 355 is dependent on the spring constant of the piston spring 243 and the integrity of the seal 235. In one embodiment, it is desired to generate a reduced pressure that is greater (i.e., a lower absolute pressure) than the amount of reduced pressure to be supplied to the tissue site. For example, if it is desired to provide 125 mmHg of reduced pressure to the tissue site, it may be desirable to have the charging chamber 355 charged to 150 mmHg of reduced pressure.

Figure 19:
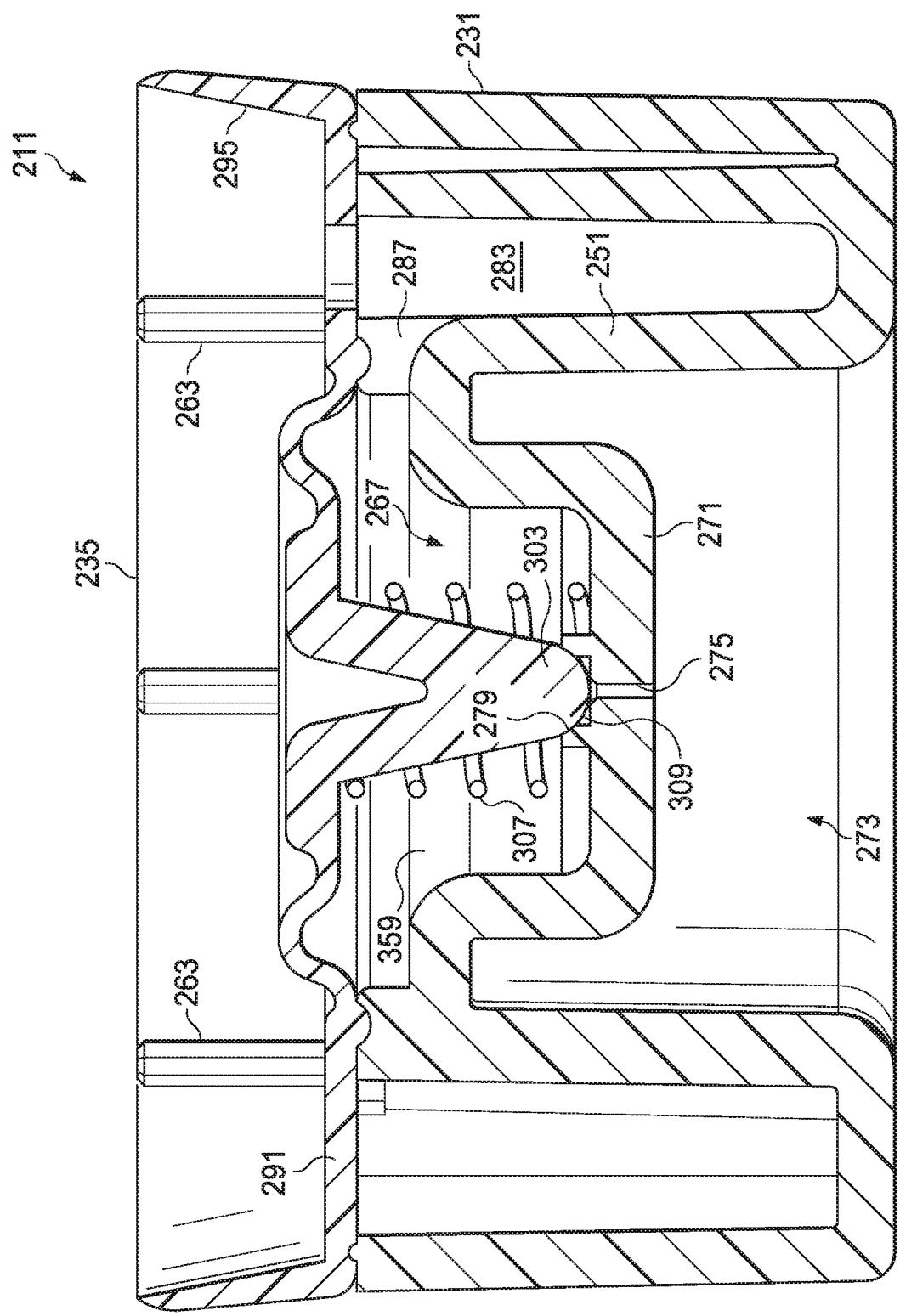
FIG. 19 illustrates an enlarged cross-sectional view of the reduced pressure treatment apparatus of FIG. 18, the reduced pressure treatment apparatus having a valve body shown in a closed position.

The regulated chamber 359 is used to generate the desired therapy pressure that is delivered to the outlet port 227 and the tissue site. When the reduced pressure within the charging chamber 355 is greater than the reduced pressure within the regulated chamber 359 and when the reduced pressure in the regulated chamber 359 is less than the desired therapy pressure, the upward force on the seal 235 (exerted by the increased absolute pressure in the regulated chamber 359 and the biasing force of the regulator spring 307, both against the atmosphere pressure exerted downward on the seal 235) moves the valve body 303 into the open position (see FIG. 20), thereby allowing fluid communication between the charging chamber 355 and the regulated chamber 359. The charging chamber 355 continues to charge the regulated chamber 359 with reduced pressure (i.e., the absolute pressure in the regulated chamber 359 continues to drop) until the reduced pressure in the regulated chamber 359, balanced against the atmospheric pressure above the seal 235, is sufficient to counteract the biasing force of the regulator spring 307 and move the valve body into the closed position (see FIG. 19). When the regulated chamber 359 is charged with the desired therapy pressure, this pressure may be delivered to the outlet port as detailed previously.

When the reduced pressure source 211 is initially connected to a delivery tube and tissue site for treatment, it will likely be necessary to compress the second barrel 219 within the first barrel 215 multiple times. As each compression stroke is completed, the reduced pressure generated within the charging chamber 355 will pull air and any other gases from the delivery tube and the tissue site until the pressure within the tube and at the tissue site begins to approach the desired therapy pressure.

As the reduced pressure source 211 is being primed by one or more compressions, it is important that air and other positively-pressurized gases being pushed out of the charging chamber 355 are pushed past the skirt portion 295 of the seal 235 and not into the regulated chamber 359. Positively pressurized gas flow to the regulated chamber 359 may transfer to the delivery tube and the tissue site, which would counteract the reduced pressure that is then being applied to the tissue site. To prevent positively pressurized gas from entering the regulated chamber 359, the shaft 347 is provided to engage the seal 235 and valve body 303. As the second barrel 219 is compressed within the first barrel 215, the second housing portion 315 moves relative to the first housing portion 311 so that the shaft 347 exerts a force on the valve body 303 that holds the valve body 303 in the closed position. Since the shaft 347 remains engaged during the entire compression, or charging stroke of the reduced pressure source 211, the air within the charging chamber 355 is vented past the seal 235 and not into the regulated chamber 359.

While the reduced pressure source 211, including the first barrel 215, the second barrel 219, the piston 231, and the seal 235, have been described herein as being cylindrical, it will be readily apparent that all of these components may be any size or shape. Additionally, the relative positions of the valve seat 279 and the valve body 303 may be varied in some embodiments.

If a dressing, delivery tube, or other component has a small leak, valve body 303 can maintain a therapeutic pressure. For example, regulated chamber 359 may be adapted to compensate for leaks that are less than about 1 L/min. However, valve body 303 may not be able to maintain the therapy pressure if a leak exceeds such a limit, which is generally dependent upon the size of the restrictions on the entry and exit sides of the regulated chamber 359.

The flow leaving regulated chamber 359 can be controlled by adjusting the bore size of regulator passage 275, and the flow coming in can be controlled by adjusting the size of the bore of a number of components in the fluid path, such as the conduit 112, tubing adapter 116, or outlet port 227. The size of the bores can be balanced such that a flow-induced drop in reduced-pressure in regulated chamber 359 deflects valve body 303, leaving a gap between valve body 303 and regulator passage 275. Thus, if a leak is increasing and exceeds a predetermined or configurable leak threshold, the decrease in reduced pressure in regulated chamber 359 may partially open valve body 303. If a leak is decreasing but exceeds the leak threshold, the drop in reduced pressure may partially close valve body 303, but still leave a gap. In some illustrative embodiments, the gap between valve body 303 and regulator passage 275 is less than 0.1 mm. Optionally, the bore sizes can be balanced so that valve body 303 remains open if no dressing is connected. Moreover, the bore sizes may be calibrated such that a flow of air through the gap produces an audible indicator, alerting an operator of an unexpected loss of therapeutic pressure. For example, a leak threshold may represent a leak rate that is sufficient to interfere with a prescribed therapy, and many applications may have a leak threshold of about 0.8 L/min. An audible indicator may be produced at this threshold if the diameter of regulator passage 275 is in the range of about 1 mm to about 1.5 mm and conduit 112 has a lumen size of about 1.2 mm over a length of about 500 mm to 800 mm. The size of the gap (e.g., the distance between apex 309 and regulator passage 275) may be calibrated so that the pitch of the audible note changes as flow decreases or increases, thereby differentiating the size or rate of a leak.

In other illustrative embodiments, the flow through the system can be controlled with additional components, such as filters, which may include membranes, sintered porous materials, fibers, woven, or non-woven materials, for example. Valve body 303 and regulator passage 275 may also be designed to accentuate the audible feedback.

Figure 21:
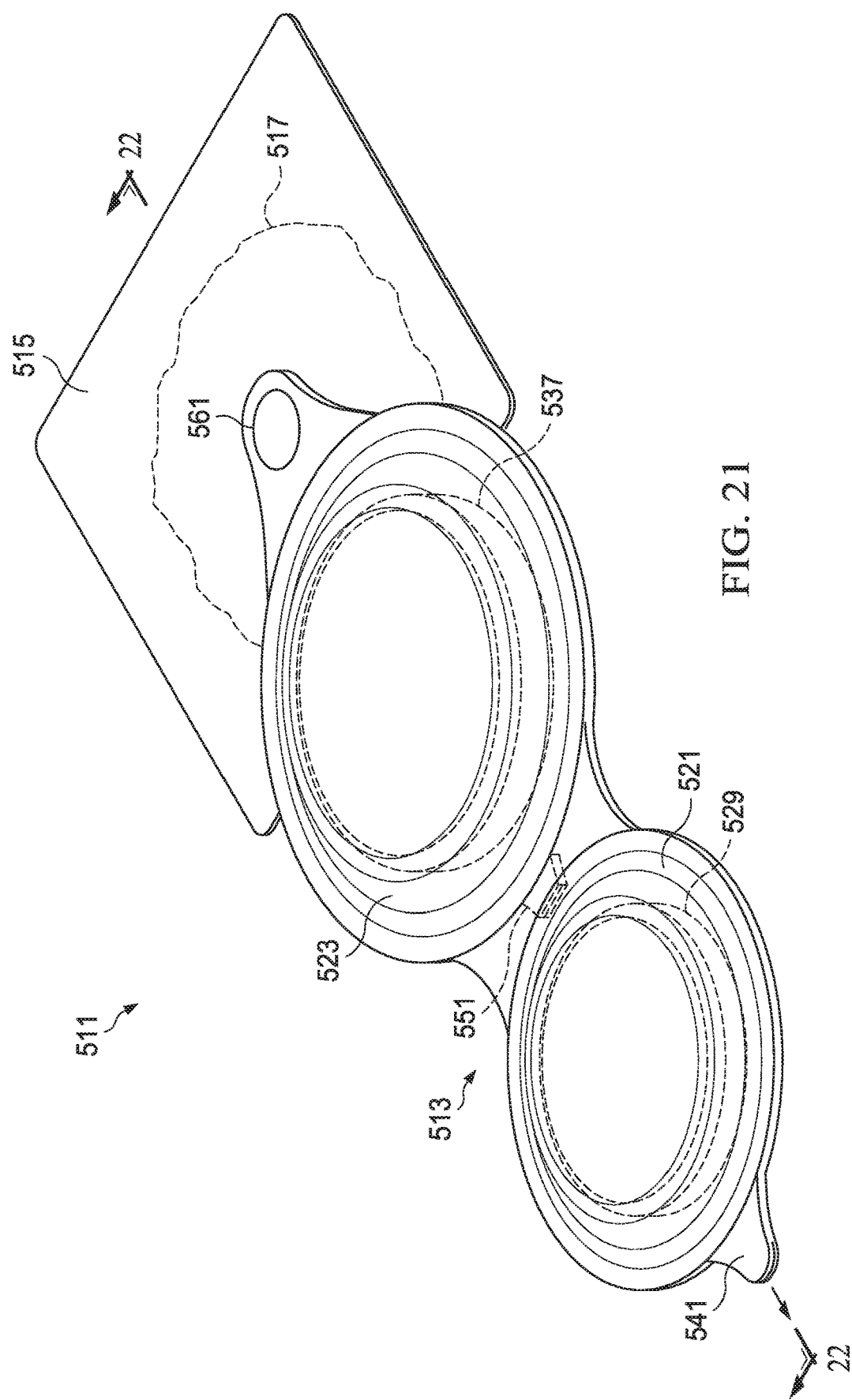
FIG. 21 illustrates a perspective view of a reduced pressure treatment apparatus according to an illustrative embodiment.
Figure 22:
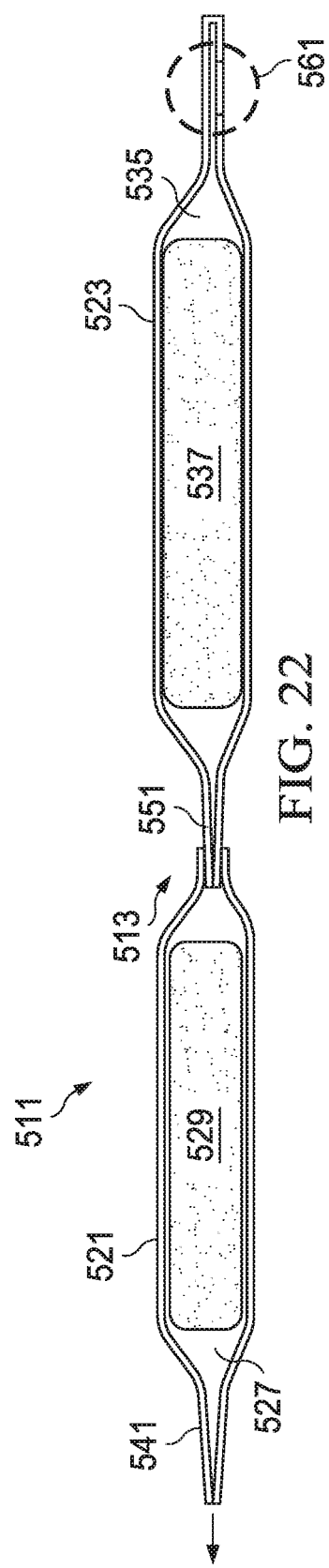
FIG. 22 depicts a cross-sectional side view of the reduced pressure treatment apparatus of FIG. 21 taken at 22-22.

Referring to FIGS. 21 and 22, a reduced pressure treatment system 511 includes a reduced pressure treatment apparatus 513 for delivering a reduced pressure to a dressing 515 positioned at a tissue site 517. The reduced pressure treatment apparatus includes a first flexible bladder 521 and a second flexible bladder 523. The flexible bladders 521, 523 are preferably made from an elastomeric material such as, for example, a silicone polymer, rubber, or another elastomeric material. The first flexible bladder 521 includes a compressible chamber 527 in which is disposed a biasing member 529. The second flexible bladder 523 includes a charging chamber 535 in which is disposed a biasing member 537. The biasing members 529, 537 may be any device that provides a biasing force to resist collapse of the chambers 527, 535. In one embodiment, the biasing members 529, 537 may be a porous foam that allows flow of fluid within or through the chambers 527, 535, but resists collapse when the chambers are exposed to a pressure less than an ambient pressure surrounding the reduced pressure treatment apparatus 513.

The first flexible bladder 521 includes a one-way valve 541 to allow expulsion of air from the compressible chamber 527 when the first flexible bladder is 521 is compressed by a user. As the biasing member 529 in the compressible chamber 527 attempts to move the first flexible bladder 521 back to an extended position, the one-way valve 541 prevents or substantially reduces fluid from entering the compressible chamber 527 through the one-way valve 541. Instead, fluid enters the compressible chamber 527 through a one-way valve 551 positioned between the first flexible bladder 521 and the second flexible bladder 523. This fluid is pulled from the charging chamber 535 into the compressible chamber 527 to create a reduced pressure within the charging chamber 535. The first flexible bladder 521 may be compressed and allowed to expand several times to create the desired amount of reduced pressure in the charging chamber 535. In one embodiment, the biasing member 537 in the charging chamber 535 is a porous foam that is more resistant to collapse than the biasing member 529 disposed in the compressible chamber 527. This configuration allows the charging chamber 535 to resist collapse such that a greater reduced pressure may be stored in the charging chamber 535.

The charging chamber 535 is positioned in fluid communication with the dressing 515 to deliver a reduced pressure to the tissue site 517. A regulator member 561 is positioned between the charging chamber 535 and the tissue site 517 to regulate pressure delivered by the charging chamber 535 to the tissue site 517. The regulator member 561 may be similar to other regulators described herein, or may be any other type of regulator or device capable of regulating pressure. In one embodiment, it is desired that a pressure within the charging chamber 535 be less than the ambient pressure and less than a desired therapy pressure that is to be delivered to the tissue site 517. The regulator member 561 ensures that pressure delivered to the tissue site 517 does not drop below the desired therapy pressure. If the pressure supplied to the tissue 517 begins to exceed the desired therapy pressure (i.e. more reduced pressure is needed), the regulator opens to allow fluid communication between the charging chamber 535 and the tissue site 517.

In the embodiment illustrated in FIGS. 21 and 22, the reduced pressure treatment apparatus has been described as having a charging chamber similar in some respects to other embodiments described herein. While a well-defined regulated chamber has not been described in this particular embodiment, a regulated chamber exists either within the dressing 515 at which regulated pressure is maintained, or within a fluid conduit fluidly connecting the regulator member 561 to the dressing 515.

Figure 23:
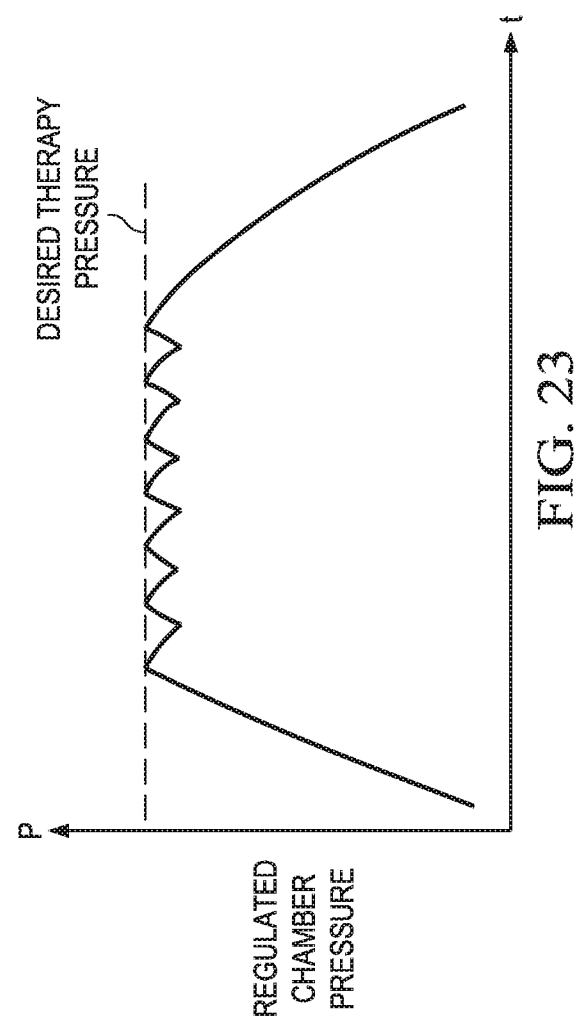
FIG. 23 illustrates a graph of regulated chamber pressure vs. time for a reduced pressure treatment apparatus.

Referring to FIG. 23, a graph is provided that illustrates the changes in pressure over time within a regulated chamber such as the regulated chambers described herein. The ability of a charging chamber to recharge the regulated chamber allows the pressure within the regulated chamber to vary little from the desired therapy pressure during operation of the reduced pressure source.

It should be apparent from the foregoing that an invention having significant advantages has been provided. While the invention is shown in only a few of its forms, it is not just limited but is susceptible to various changes and modifications without departing from the spirit thereof.

What is claimed is:

1. A reduced-pressure treatment apparatus for delivering a reduced pressure to a dressing positioned at a tissue site, the reduced-pressure treatment apparatus comprising:
   a first flexible bladder having a compressible chamber;
   a first biasing member disposed in the compressible chamber;
   a first one-way valve fluidly coupled to the first flexible bladder;
   a second flexible bladder having a charging chamber configured to be fluidly coupled to the dressing;
   a second biasing member disposed in the charging chamber;
   a second one-way valve fluidly coupled to the first flexible bladder and the second flexible bladder;
   wherein compression of the first flexible bladder draws fluid from the charging chamber, developing a reduced pressure in the charging chamber.

2. The reduced-pressure treatment apparatus of claim 1, where the first flexible bladder and the second flexible bladder are formed from an elastomeric material.

3. The reduced-pressure treatment apparatus of claim 1, wherein the first flexible bladder and the second flexible bladder are formed form at least one of a silicone polymer and rubber.

4. The reduced-pressure treatment apparatus of claim 1, wherein the first biasing member and the second biasing member comprise a porous foam.

5. The reduced-pressure treatment apparatus of claim 4, wherein the porous foam is configured to distribute fluid through the porous foam and resist collapse if exposed to a pressure less than an ambient pressure surrounding the reduced-pressure treatment apparatus.

6. The reduced-pressure treatment apparatus of claim 1, wherein the first one-way valve is configured to permit flow of fluid out of the compressible chamber and to prevent fluid flow into the compressible chamber through the first one-way valve.

7. The reduced-pressure treatment apparatus of claim 1, wherein the second one-way valve is configured to permit fluid flow from the charging chamber to the compressible chamber and to prevent fluid flow from the compressible chamber to the charging chamber.

8. The reduced-pressure treatment apparatus of claim 1, wherein the second biasing member is stiffer than the first biasing member.

9. The reduced-pressure treatment apparatus of claim 1, further comprising a regulator fluidly coupled between the charging chamber and the dressing.

10. The reduced-pressure treatment apparatus of claim 9, wherein the regulator comprises:
    a regulator passage between the charging chamber and the dressing;
    a valve body adapted to control fluid communication through the regulator passage; and
    a regulator spring engaged with the valve body to bias the valve body against a differential between a pressure in the dressing and an ambient pressure.

11. The reduced-pressure treatment apparatus of claim 10, wherein the regulator passage has a bore size adapted to deflect the valve body to cause an audible indication of a leak that exceeds a predetermined threshold.

12. A reduced-pressure treatment system for delivering a reduced pressure to a tissue site, the reduced-pressure treatment system comprising:
    a dressing configured to be positioned adjacent the tissue site;
    a reduced-pressure treatment apparatus configured to be fluidly coupled to the dressing, the reduced-pressure treatment apparatus comprising:
      a first flexible bladder having a compressible chamber;
      a first biasing member disposed in the compressible chamber;
      a first one-way valve fluidly coupled to the first flexible bladder;
      a second flexible bladder having a charging chamber configured to be fluidly coupled to the dressing;
      a second biasing member disposed in the charging chamber;
      a second one-way valve fluidly coupled to the first flexible bladder and the second flexible bladder;
      wherein compression of the first flexible bladder draws fluid from the charging chamber, developing a reduced pressure in the charging chamber.

13. The reduced-pressure treatment system of claim 12, wherein the first biasing member and the second biasing member comprise a porous foam configured to distribute fluid through the porous foam and resist collapse if exposed to a pressure less than an ambient pressure surrounding the reduced-pressure treatment apparatus.

14. The reduced-pressure treatment system of claim 12, wherein the first one-way valve is configured to permit flow of fluid out of the compressible chamber and to prevent fluid flow into the compressible chamber through the first one-way valve.

15. The reduced-pressure treatment system of claim 12, wherein the second one-way valve is configured to permit fluid flow from the charging chamber to the compressible chamber and to prevent fluid flow from the compressible chamber to the charging chamber.

16. The reduced-pressure treatment system of claim 12, wherein the second biasing member is stiffer than the first biasing member.

17. The reduced-pressure treatment system of claim 12, further comprising a regulator fluidly coupled between the charging chamber and the dressing, the regulator comprising:
   a regulator passage between the charging chamber and the dressing;
   a valve body adapted to control fluid communication through the regulator passage; and
   a regulator spring engaged with the valve body to bias the valve body against a differential between a pressure in the dressing and an ambient pressure.

18. The reduced-pressure treatment system of claim 17, wherein the regulator passage has a bore size adapted to deflect the valve body to cause an audible indication of a leak that exceeds a predetermined threshold.

19. A method for treating a tissue site with reduced pressure, the method comprising:
   providing a reduced-pressure treatment apparatus comprising:
      a first flexible bladder having a compressible chamber;
      a first biasing member disposed in the compressible chamber;
      a first one-way valve fluidly coupled to the first flexible bladder;
      a second flexible bladder having a charging chamber;
      a second biasing member disposed in the charging chamber;
      a second one-way valve fluidly coupled to the first flexible bladder and the second flexible bladder;
   fluidly coupling the charging chamber of the reduced-pressure treatment apparatus to a dressing disposed adjacent to a tissue site;
   compressing the first flexible bladder to draw fluid from the charging chamber of the second flexible bladder, thereby generating a reduced-pressure in the charging chamber; and
   communicating the reduced-pressure in the charging chamber to the dressing.

20. The method of claim 19, further comprising:
   providing a regulator;
   fluidly coupling the regulator between the charging chamber and the dressing; and
   regulating the reduced pressure communicated to the dressing to maintain the dressing at a therapy pressure.

* * * * *

UNITED STATES PATENT AND TRADEMARK OFFICE
CERTIFICATE OF CORRECTION

| | |
|---|---|
| PATENT NO. | : 10,786,607 B2 |
| APPLICATION NO. | : 15/875110 |
| DATED | : September 29, 2020 |
| INVENTOR(S) | : Locke et al. |

Page 1 of 1

It is certified that error appears in the above-identified patent and that said Letters Patent is hereby corrected as shown below:

On the Title Page

Page 3, Column 1
Line 7, delete "Philidelphia," and insert -- Philadelphia, --, therefor.

Page 3, Column 2
Line 45, delete "Hypermia" and insert -- Hyperemia --, therefor.

In the Specification

Column 6
Line 40, delete "capralactones." and insert -- caprolactones. --, therefor.
Line 49, delete "hydroxy apatites," and insert -- hydroxyapatites, --, therefor.

Column 7
Line 5, delete "by" and insert -- be --, therefor.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*